US007785870B2

(12) United States Patent
Takahashi et al.

(10) Patent No.: US 7,785,870 B2
(45) Date of Patent: Aug. 31, 2010

(54) CELL-SPECIFIC EXPRESSION/REPLICATION VECTOR

(75) Inventors: Katsuhito Takahashi, Ikeda (JP); Hisako Yamamura, Ikoma (JP)

(73) Assignee: Japan Science and Technology Agency, Saitama (JP)

( * ) Notice: Subject to any disclaimer, the term of this patent is extended or adjusted under 35 U.S.C. 154(b) by 58 days.

(21) Appl. No.: 10/500,173

(22) PCT Filed: Dec. 26, 2002

(86) PCT No.: PCT/JP02/13683

§ 371 (c)(1),
(2), (4) Date: Jun. 24, 2004

(87) PCT Pub. No.: WO03/057888

PCT Pub. Date: Jul. 17, 2003

(65) Prior Publication Data

US 2005/0032214 A1 Feb. 10, 2005

(30) Foreign Application Priority Data

Dec. 28, 2001 (JP) .............................. 2001-402102
Aug. 30, 2002 (JP) .............................. 2002-255395

(51) Int. Cl.
*C12N 15/00* (2006.01)
*A61K 31/70* (2006.01)
(52) U.S. Cl. .................................. 435/320.1; 514/44 R
(58) Field of Classification Search ....................... None
See application file for complete search history.

(56) References Cited

U.S. PATENT DOCUMENTS 5,728,379 A * 3/1998 Martuza et al. ............. 424/93.2
6,649,158 B1 * 11/2003 LaFace ...................... 424/93.2
2004/0197308 A1 * 10/2004 Takahashi et al. ........... 424/93.2
2005/0074430 A1 * 4/2005 Van Meir et al. ............ 424/93.2

FOREIGN PATENT DOCUMENTS

JP         2002-335965        11/2002

OTHER PUBLICATIONS

Chung et al., J Virol, 1999, 73: 7556-7564.*
Tjuvajev et al., Cancer Res, 1998, 58: 4333-4341, Abstract.*
Borisy et al., Proc Natl Acad Sci USA, 2003, 100: 7977-7982.*
El-Aneed et al., European Journal of Pharmacology, 2004, 498: 1-8.*
Keith et al., Nature Reviews, 2005, 4: 1-8.*
Everts et al., Cancer Gene Therapy, 2005, 12: 141-161, Review.*
Meng et al., Gene Therapy of Cancer, Chapter 1, 1999, pp. 3-20.*
Vargese et al., Cancer Gene Therapy, 2002, 9: 967-978, Review.*
Van Dyke et al., Cell, 2002, 108: 135-144.*
Hardcastle et al., Current Cancer Drug Targets, 2007, 7: 181-189.*
Miyatake, Human Cell, 2002, 15: 130-137.*
Miyatake et al., Stroke, 1999, 30: 2431-2439.*
Wagstaff et al., Gene Therapy, 1998, 5: 1566-1570.*
Foster et al., J Virol Methods, 1998, 75: 151-160.*
Cheon, J. et al., "Adenovirus-mediated suicide-gene therapy using the herpes simplex virus thymidine kinase gene in cell and animal models of human prostate cancer: changes in tumour cell proliferative activity," *BJU International*, 85:6, pp. 759-766, Apr. 2000.
Takahashi, K. et al., "Transcriptional Targeting of Replication-Competent Herpes Simplex Virus to Proliferating Smooth Muscle Cells," *Circulation*, Supplement II, 102:18, Oct. 31, 2000.
Takashi, K., et al., "The 5'-Flanking Region of the Human Smooth Muscle Cell Calponin Gene Contains a *cis*-Acting Domain for Interaction with a Methylated DNA-Binding Transcription Repressor," *J. Biochem*, 120:1, pp. 18-21, Jul. 1996.
Yamamura, Hisako et al., "Identification of the Transcriptional Regulatory Sequences of Human Calponin Promoter and Their Use in Targeting a Conditionally Replicating Herpes Vector to Malignant Human Soft Tissue and Bone Tumors," *Cancer Research*, 61:10, pp. 3969-3977, May 15, 2001.
Krüger, M. et al., "Involvement of Proteasome α-Subunit PSMA7 in Hepatitis C Virus Internal Ribosome Entry Site-Mediated Translation," *Molecular and Cellular Biology*, 21:24, pp. 8357-8364, Dec. 2001.
Takahashi, Yamamura, "Development of Novel Targeting Gene Therapy for Intractable Sarcoma," Genetic Medicine, vol. 5, No. 4, 2001. Japanese publication submitted with English translation of related sections.
English Translation of Japanese Office Action for corresponding Japanese application No. JP2002-255395, issued Dec. 8, 2006.
Hunter et al., "Attenuated, Replication-Competent Herpes Simplex Virus Type 1 Mutant G207: Safety Evaluation of Intracerebral Injection in Nonhuman Primates," *Journal of Virology*, vol. 73, No. 8, pp. 6319-6326, Aug. 1999.
Martuza, Robert L., "Conditionally replicating herpes vectors for cancer therapy," *The Journal of Clinical Investigation*, vol. 105, No. 7, pp. 841-846, Apr. 2000.
Mineta et al., "Attenuated multi-mutated herpes simplex virus-1 for the treatment of malignant gliomas," *Nature Medicine*, vol. 1, No. 9, pp. 938-943, Sep. 1995.
European Search Report cited in a counterpart European Patent Application No. EP 02 790 914.2, date of completion of the Search Report: Feb. 19, 2009.

*Primary Examiner*—Ileana Popa
(74) *Attorney, Agent, or Firm*—Locke Lord Bissell & Liddell LLP

(57) ABSTRACT

The present invention provides a cell-specific expression/replication vector, and a method of treatment comprising introducing a cell-specific expression/replication vector into specific cells such as malignant tumors in order to selectively disrupt the specific cells. A vector according to the invention is constructed by: obtaining a transcriptional initiation regulatory region of human calponin gene that is specifically expressed in smooth muscle cell; linking the above region upstream to a replication-related gene of a virus such as ICP4 and the like; linking DNA that encodes a protein such as suppressive factor for tumor angiogenesis or apoptosis-related factors and the like via IRES to the replication-related gene of the virus; and integrating a thymidine kinase gene in an intact state into the viral DNA.

10 Claims, 9 Drawing Sheets

OTHER PUBLICATIONS

Akyürek et al. "SM22α Promoter Targets Gene Expression to Vascular Smooth Muscle Cells In Vitro and In Vivo,"*Molecular Medicine*, vol. 6, No. 11, pp. 983-991, Nov. 2000.

Miyatake et al. "Inhibition of Rat Vascular Smooth Muscle Cell Proliferation In Vitro and In Vivo by Recombinant Replication-Competent Herpes Simplex Virus," *Stroke*, vol. 30, pp. 2431-2439, Nov. 1999.

Supplementary Partial European Search Report cited in European application No. EP 02 79 0914, date of completion of the Search Report: Jul. 5, 2006.

* cited by examiner

CELL-SPECIFIC EXPRESSION/REPLICATION VECTOR

TECHNICAL FIELD

The present invention, in various embodiments, relates to a cell-specific expression/replication vector, which does not target normal self-replicating cells and expresses a cell-specific gene. Particularly, the present invention in one embodiment relates to a cell-specific expression/replication vector that is capable of suppressing expression/replication at a desired period after its expression/replication. In another embodiment, the present invention relates to a method for expressing a gene in a specific cell in a living organism by using the cell-specific expression/replication vector, or a method for disrupting a specific cell by using the cell-specific expression/replication vector.

More specifically, the present invention relates to, in one embodiment, the construction of a cell-specific expression/replication vector designed for gene therapy of cancer. The expression/replication vector can express cell-specific genes to specifically disrupt a particular cancer cell or a proliferating smooth muscle cell in the new tumor blood vessel, which allows treatment without injuring normal cells and completely eliminate the vector-infected cells after the therapy is finished.

In another embodiment, the present invention relates to the construction of cell-specific expression/replication vector designed for gene therapy against fibrosis such as pulmonary fibrosis and hepatic fibrosis. The expression/replication vector can express cell-specific genes to specifically disrupt proliferating myofibroblasts, which allows treatment without injuring normal cells and can completely remove the vector-infected cells after the therapy is finished.

In yet another embodiment, the present invention relates to the construction of cell-specific expression/replication vector designed for gene therapy of vessel constriction, restenosis, diabetic retinopathy and the like after stent placement or organ transplantation, arteriosclerosis and diabetic retinopathy. The expression/replication vector can express cell-specific genes to specifically disrupt proliferating vascular smooth muscle cells, which allows treatment without injuring normal cells and can completely remove the vector-infected cells after the therapy is finished.

In yet another embodiment, the present invention relates to the construction of cell-specific expression/replication vector designed for gene therapy for glomerulonephritis, wherein the expression/replication vector can express cell-specific genes that specifically disrupt proliferating mesangial cells.

Each embodiment of present invention allows treatment without injuring normal cells and can completely remove the vector-infected cells after the therapy is finished.

BACKGROUND ART

Recently, an ideal therapeutic method for cancer, with less side effects, has been desired, wherein normal cells are not affected and only the cancer cells can be selectively impaired. For example, gene therapy is capable of increasing the selectivity of the cancer cell at various levels, such as the cell selectivity and expression promoter activity of a gene to be introduced into the cancer cell, or infection and induction method of a viral vector. However, there is a common problem. Since expression of a tissue-specific differentiation antigen in the immunotherapy for cancer is also observed to some extent in normal cells, the side effects to the normal cells pose a problem. Furthermore, since cancer antigen with a mutation is limited to the individual cancers, it is not suitable as an immunotherapy for cancer that is molecule-targeted.

Recently, a clinical study of gene therapy was conducted to treat a malignant brain tumor using a replication-competent herpes simplex virus (HSV) (vector) that continuously and selectively impairs only the proliferating cells by infection and replication (*Gene Ther.* 7, 859-866, 2000; *Gene Ther.* 7, 867-874, 2000). The replicative HSV vector is a vector with deleted Ribonucleotide reductase (RR) or Thymidine kinase (TK) that are essential for viral replication. These enzymes express in normal cells only when they are proliferating but express constitutively in tumor cells. Therefore, when this HSV vector infects a cell that proliferates strongly, regardless whether it is a normal cell or a tumor cell, it replicates with cell-derived RR or TK and shows a cytolytic activity. Meanwhile, an anti-tumor effect of replicative HSV vectors against prostate cancer and pancreatic cancer has also been reported in an animal experiment (*J. Surg. Oncol.* 72, 136-141, 1999), however, these vectors do not have cell selectivity either, and their safety is low. Therefore, while such a vector could be used in therapy of human brain tumors, since this vector does not diffuse into the circulating blood due to the presence of a blood brain barrier, it is not suitable for treatment in any other organs.

Thus, a further effective and safer therapy can be implemented if the impairment activity of the HSV vector is controlled target in cell-specifically. Martuza et al. reported on a replication-competent HSV vector that is liver tumor-selective, using an albumin promoter (*J. Virol.* 71, 5124-5132, 1997). However, when this vector is used in liver cell cancer, the expression of albumin gene decreases and the normal regenerative liver cells are also impaired. Therefore, it is not considered suitable for clinical application in human. The description of U.S. Pat. No. 5,728,379 ("Tumor- or cell-specific herpes simplex virus replication") mentions the possibility of application of this system to mesothelioma, however, it does not state the possibility of application to therapies for human sarcoma in general, such as leiomyosarcoma, osteosarcoma, gastrointestinal stromal tumor (GIST), tumor vessel, proliferating vascular lesion, proliferating glomerulonephritis, fibrosis of lung, liver and the like, or myofibroblast that proliferate at the stroma of malignant tumors.

The existence of fusion gene and mutation of p53 and Rb in some tumors are reported based on the genetic analysis of the disease cause and pathology of sarcoma, with yet limited applicability to therapies. In an animal experiments using nude mice, Milas et al. employed an adenoviral vector without a replication ability to introduce p53 gene into leiomyosarcoma cells, and reported that a delayed effect in the proliferation of tumors (*Cancer Gene Ther.* 7, 422-429, 2000). A method for introducing and expressing a suicide gene, thymidine kinase, into osteosarcoma by using an osteocalcin gene promoter has also being described (*Cancer Gene Ther.* 5, 274-280, 1998). However, it uses a viral vector with no replication ability which results in the poor efficiency for gene transfer Such system, therefore, cannot be applied to sarcoma other than osteosarcoma. Particularly, according to Milas et al., a human smooth muscle cell line (SK-LMS-1) were infected with 100 to 1000 fold more amount of viral particles with lower efficiency in comparison to the amount of particles of the viral vector used in the report (*Cancer Res.* 61, 3969-3977, 2001) by the present inventors. Therefore, the approach of Milas et al. is not preferable, from the viewpoint of suppressing the side effects by minimizing the number of viral particles to be injected into the body.

Furthermore, Folkman, et al. reported a dramatic anti-tumor effect of anti-angiogenesis peptides such as angiostatin and endostatin in mice as a therapy for suppressing angiogenesis of cancer (*Cell* 79, 315-328, 1994; *Cell* 88, 277-285, 1997). Nakamura et al. also reported the suppressing action of angiogenesis of NK4, an intramolecular fragment of a hepatocyte growth factor (HGF) (*Biochem. Biophys. Res. Commun.* 279, 846-852, 2000). However, these methods have problems, such as (1) the requirement for a large amount of peptides, (2) their reproducibility to endostatin is low, (3) the mechanism is unknown, and (4) the efficacy in human has not been confirmed. The inhibitor of angiogenesis, which is currently in clinical trial, does not have cell selectivity and its inhibiting efficiency is low. The peptide which inhibits the action of the integrin on the surface of endothelial cells, reported by Cheresh et al., does not have cell selectivity as well, and its inhibiting efficiency is low (*J. Clin. Invest.* 103, 1227-1230, 1999). These studies all relate to therapies that target vascular endothelial cells, however, cell-selective therapeutic agent targeting tumor vessel composed of proliferating vascular smooth muscle cells has not been known. In fact, it is reported that the antagonist of a platelet-derived growth factor receptor that facilitates the proliferation and migration of smooth muscle cells has a strong suppressing action for tumor angiogenesis (*Cancer Res.* 60, 4152-4160, 2000), and the importance to attack the vascular smooth muscle in order to suppress the tumor angiogenesis is speculated. However, this method is not cell-selective and side effects are also expected.

Moreover, various agents that suppress the proliferation of smooth muscles of neointima have been examined for the proliferating vascular lesion, in particular, vessel constriction after stent placement and heart transplantation. However, none of these agents have succeeded in preventing constriction. As a recent attempt in gene therapy, there is a report by Leiden et al., to selectively introduce a LacZ gene into a smooth muscle cells of a rat carotid artery after balloon injury, under the control of a promoter of SM22a, a homologous gene of calponin using an adenoviral vector that is deficient in replication ability (*J. Clin. Investi.* 100, 1006-1014, 1997). However, in this experiment, it was not the proliferating smooth muscle of the intima that is a target cell, but the smooth muscle of the tunica media that was introduced with the LacZ gene, and the efficiency of introduction was extremely low. Further, Nabel et al. also conducted an experiment using an adenoviral vector without a replication ability, wherein a LacZ gene and CAT (chloramphenicol acetyltransferase) gene were introduced into pig artery under the control of SM22a prompoter. However, only 2.2% of the intimal smooth muscle cells, 0.56% of the tunica media smooth muscle cells showed gene expression (*Mol. Med.* 6, 983-991, 2000). In contrast, according to Miyatake et al., the replication of HSV virus, which was used to infect rat carotid artery after balloon injury, is observed mainly in the proliferating smooth muscles of the intima, and the efficacy of using a replicative viral vector is speculated (*Stroke* 30, 2431-2439, 1999). However, this virus is not cell-selective and side effects such as the cell disruption of intima cells and adventitial fibroblasts are expected. Other methods such as directly introducing decoy and antisense DNA oligonucleotide into the vessel have also been attempted, however, the efficiency of introduction is low and sufficient suppressive effect of vessel smooth muscle proliferation is unlikely.

In another recent attempt of gene therapy based on proliferating mesangial cells in glomerulonephritis, a method has been reported wherein decorin and TGFB receptor are introduced into the renal glomerulus using a liposome vector. The receptors inhibit TGFβ1 and chimeric gene of the IgG Fc region, or decoy of NFkappaB (*Nature Med.* 2, 418-423, 1996; *Kidney Int.* 55, 465-475, 1999; *Gene Ther.* 7, 1326-1332, 2000). However, this method is not cell-selective and side effects are also expected. Moreover, a method has been presented, wherein an adenoviral vector deficient in replication ability is bound to a microsphere of polystyrene and administered to a rat aorta, in order to selectively introduce a gene into a renal glomerulus (*Kidney Int.* 58, 1500-1510, 2000). However, aside from mesangial cells, which are a cause for proliferating glomerulonephritis, expression of introduced genes is observed also in vascular endothelial cells. Further, the immunogenicity of adenovirus is strong, and there is a high risk for it to evoke the immune response that leads to glomerulonephritis (*Kidney Int.* 61, S85-S88, 1997).

Meanwhile, the present inventors have found that a calponin gene, which is thought to be a differentiation marker of smooth muscles, is expressed in the tumor cells of human-derived sarcoma (*Int. J. Cancer* 79, 245-250, 1998; *Sarcoma* 3, 107-113, 1999; *Intern. J. Cancer* 82, 678-686, 1999). Thereafter, there have been continuous reports that calponin genes express abnormally in almost 20 types of human malignant tumor derived from mesenchymal cells such as bone sarcoma and soft tissue sarcoma as well as in gastrointestinal stromal tumor (GIST) and salivary gland sarcoma, fibrosarcoma, malignant neurinoma. The X-ray crystallographic structure and the in vitro and in vivo functional analyses of the calponin (h1 or basic) revealed that calponin binds to the C-terminal region of actin molecules and suppresses the sliding motility of actin and myosin (*Biochem. Biophys. Res. Commun.* 279, 150-157, 2000; *J. Physiol.* 529, 811-824, 2000). In an adult body, the calponin gene selectively expresses in the smooth muscle cell and is regarded as a differentiation marker of the vessels and gastrointestinal tract (*Physiol. Rev.* 75, 487-517, 1995).

U.S. Pat. No. 5,728,379 mentioned above and the report by the present inventors (*Cancer Res.* 61, 3969-3977, 2001) further describe a replicative vector deficient in a DNA that encodes a thymidine kinase of HSV. However, HSV deficient in thymidine kinase is not sensitive to aciclovir or ganciclovir, which are anti-herpes virus agents, and when these vectors are applied in therapies for human, there would be serious safety concerns if the expansion of unexpected infection of the virus occurs.

In a recent study a replication-competent HSV-1, G207, has been prepared. The vector is deficient in both copies of the gamma 34.5 gene that are involved in the replication in the neuronal cells, has the LacZ gene inserted in the ribonucleotide reductase (ICP6)-locus (*Nature Med.* 1, 938-943, 1995). Another replication-competent HSV-1 vector HSV1yCD has an autofluorescent protein and a cytosine deaminase that are expressed by a CMV promoter/enhancer inserted in the ICP6-locus by homologous recombination (*Cancer Res.* 61, 5447-5452, 2001). However, since both are deficient in ribonucleotide reductase, it is anticipated that both vectors would replicate in proliferating cells alone but there would be no cell selectivity. Moreover, there is no report of a treatment method wherein the proliferating myofibroblast in the fibrosis such as pulmonary fibrosis and hepatic fibrosis is targeted and selectively disrupted. In addition, there have been no report of a treatment method wherein the myofibroblast that proliferate of malignant tumors are targeted.

SUMMARY OF INVENTION

The object of the present invention is to construct a cell-specific expression/replication vector for use in the treatment/ therapy of malignant tumors and the like, where genes are exclusively expressed and replicated in specific cells. Normal cells are not injured by such vector and the expression and replication of such vectors can be specifically suppressed at a desired period after the start of expression/replication. The object of the present invention is to provide a treatment method where said vector is introduced into the cells of specific organisms such as malignant tumor and the like and then expressed.

A cell-specific expression/replication vector of the present invention, that does not act in adult normal cells and can induce viral replication is constructed by the following steps. (1) Obtain a region that regulates the transcription initiation of a human calponin gene that specifically expresses in tumor cells and smooth muscle cells. (2) Said region is integrated to the upstream of the gene that encodes the transcription factor necessary to initiate the expression of the viral replication-related gene. (3) Said gene is expressed in specific cells such as malignant tumor cells or proliferating smooth muscle cells of new vessels in the tumors and in the lesions of vascular constriction by substituting this with a TK gene that is an essential enzyme for the replication of viral DNA. When the constructed cell-specific expression/replication vector was introduced into a malignant tumor tissue, the tumor cells and the proliferating smooth muscles of the new vessels in the tumors and in the lesions of vascular constriction are selectively impaired (*Cancer Res.* 61, 3969-3977, 2001; Japanese Patent Application No. 2001-143999).

Up to now, the HSV-1 vector that is cell-specific has been demonstrated to have a calponin promoter (*Cancer Res.* 61, 3969-3977, 2001; Japanese Patent Application No. 2001-143999) or an albumin promoter that is liver tumor-selective (*J. Virol.* 71, 5124-5132, 1997; U.S. Pat. No. 5,728,379). However, their parent strain is an HSV-1 mutant virus d120 that is deficient in genes that encode ICP4, an essential transcription factor for viral replication. Moreover, LacZ cDNA is linked upstream of the promoter and ICP4 cDNA is linked downstream of the promoter, and thymidine kinase locus (TK-locus) is disrupted by homologous recombination. Therefore, the expression of LacZ gene that serves as a marker in the process of vector purification is under control of the TK gene promoter.

The replication-competent HSV-1 vector with deficiency in thymidine kinase lacks sensitivity to aciclovir and ganciclovir, which are anti-herpes virus agents. Therefore, the method for purifying the vector to a single clone had been conducted by repeating cycles for plaque purification. The method includes the steps of: (1) infecting a Vero E5 cell with a virus mixed solution after homologous recombination, wherein ICP4 cDNA was introduced; (2) isolating multiple plaques by blue staining, which indicates the expression of LacZ genes in a 5-bromo-4-chloro-3-indolyl-β-D-galactopyranoside (X-gal) agarose overlay assay; (3) if the Vero E5 cells are infected, the steps are repeated again in the presence of ganciclovir. However, the method for elimination of the virus by the anti-herpes virus drug can not be used if the recombination at the TK-locus has not occurred. Specifically, the methods for purification used in the virus lacking a TK gene, cannot be applied in the purification of a cell-specific expression/replication vector having a TK gene. In addition, it is impossible to isolate a single plaque at the initial stage of screening, in the method of X-gal agarose overlay assay.

At the point when the agarose is overlaid, the division and proliferation of the cells stop as well as the replication of the virus, and the amount of viral particles does not increase thereafter. Hence, in the case of a replication-competent vector having a LacZ gene that is expressed by a promoter with an activity stronger than the TK gene promoter (for example, by the promoter of ribonucleotide reductase (RR) gene) if the replication ability of the vector itself is not high and the vector is stained blue in the same level as that of the replication-competent vector having a LacZ gene that is expressed by the promoter of TK gene, the number of virus per cell would be few. For that reason, it is difficult to isolate the vector with replication ability for the next screening.

Further, when an ICP4 cDNA is linked to the optional gene inserted downstream of the IRES (internal ribosomal entry site) (a CDNA that express for example Green Fluorescent Protein), the optional gene is expressed under the control of a cell-specific transcriptional initiation regulatory region. Thus, screening using the expression of both the optional gene and the LacZ gene as an index becomes possible, and the present inventors discovered that the viral vector can be separated more definitely and rapidly once the homologous recombination successfully occurs at the desired location of the vector.

Further, the present inventors discovered that a vector can be selected and concentrated by the following method once the objective recombination occurs, i.e., the ICP4 is expressed under the control of a cell-specific promoter: (1) in the first screening after the homologous recombination, a virus is infected to an ICP4 non-expressing cell wherein the virus has the promoter of the gene that express in a specific cell, i.e., the transcriptional initiation regulatory region. The virus can be activated/infected an ICP4 non-expressing cell that expresses said cell-specific gene and the virus is replicated and proliferated; (2) then the gene which is integrated in the vector is expressed, which serves as an index in purification until a single clone is obtained by limiting dilution. Further, in the cell-specific expression/replication vector of the instant invention, thymidine kinase is preserved and the virus can be inactivated and extinguished with its infected cells by the treatment with aciclovir and the ganciclovir. There is an excellent property in the safety measures of preventing the unexpected expansion of infection of the virus. Whereas, the invention of the U.S. Pat. No. 5,728,379 and Japanese Patent Application No. 2001-143999, which is a cell-specific replicative HSV-1 vector with deficient thymidine kinase can be considered as not applicable to the therapies for human. The present inventors confirmed by in vitro cell culture system or animal experiment system that the cell-specific expression/replication vector has a therapeutic effect against malignant fibrous histiocytoma (MFH) which actually appears most frequently among the human soft tissue sarcoma, gastrointestinal stromal tumor (GIST) which appears most frequently among the human gastrointestinal sarcoma, and uterine myoma which appears most frequently among the field of gynecology.

DISCLOSURE OF THE INVENTION

Figure 1:
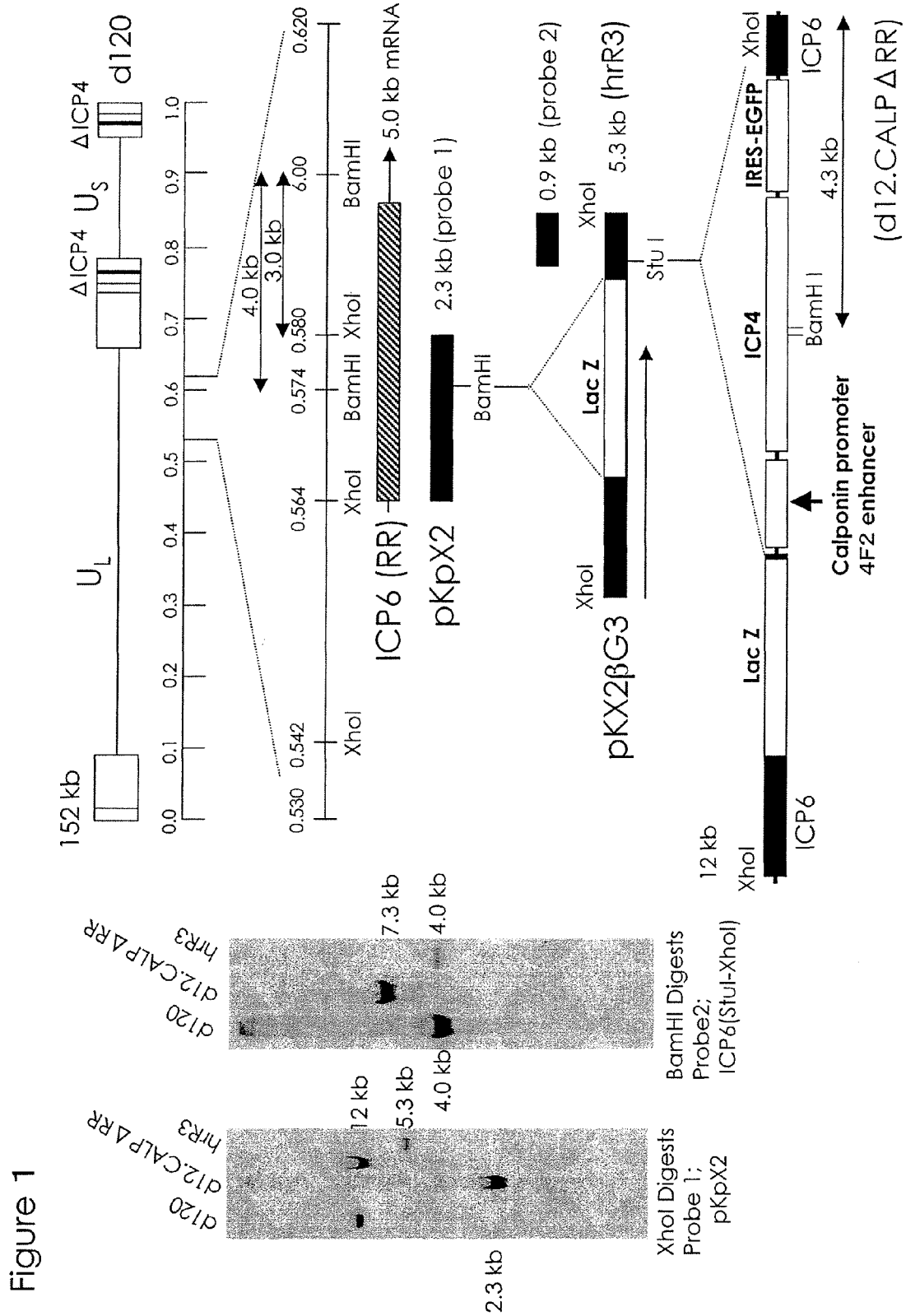
FIG. 1 shows the procedure of constructing d12•CALPΔRR and its structure. The view on the left shows the results of Southern blot wherein pKpX2 (XhoI fragment of ICP6) and StuI-XhoI fragment of ICP6 are used as DIG-labeled probes. d120 is a parental strain wherein homologous recombination is conducted, and is a mutant derived from KOS strain wherein both of the two of ICP4 genes are deficient. In hrR3, ICP6 is deleted as a result of introducing a LacZ gene in the BamHI site of the ribonucleotide reductase (ICP6) gene of KOS strain (pKX2βG3), which is a wild-type strain.

The present invention, in one embodiment, relates to: a cell-specific expression/replication vector that does not target adult normal cells. Another embodiment relates to the cell-specific expression/replication vector where a transcriptional initiation regulatory region of a gene specifically expressed in cells is integrated upstream of a predetermined gene, and a thymidine kinase gene is used to suppress the replication at a desired period; where the transcriptional initiation regulatory region of the gene that expresses cell-specifically is a region including the base sequence of Seq. ID No. 1; where the region including the base sequence of Seq. ID No. 1 is a region including a human calponin gene promoter comprising a base sequence of Seq. ID No. 2; where the region including a base sequence of Seq. ID No. 2 is a region including a base sequence of Seq. ID No. 3; where the transcriptional initiation regulatory region of the gene that expresses cell-specifically comprises a base sequence wherein one or a few base is deleted, substituted or added in a base sequence of Seq. ID No. 1, Seq. ID No. 2 or Seq. ID No. 3, and is a region including a base sequence having a transcription initiation control activity; where an enhancer is integrated upstream of the transcriptional initiation regulatory region; where the enhancer is a 4F2 enhancer; where a DNA that encodes a desired protein different from the predetermined gene is linked further downstream on the predetermined gene, and expresses the desired protein under the control of said transcriptional initiation regulatory region; where the DNA that encodes the desired protein is linked to the predetermined gene via an IRES (internal ribosomal entry site); where the DNA that encodes the desired protein is an apoptosis promotion-related gene; where the DNA that encodes a protein having action to suppress angiogenesis; where the DNA that encodes a protein having action to suppress cancer metastasis; where the DNA that encodes a protein having action to suppress cancer growth; where the predetermined gene is a viral replication-related gene; where the viral replication-related gene is ICP4 or E1A; where the expression/replication vector is a viral vector; where the viral vector is a herpes simplex virus vector (HSV vector) or an adenoviral vector; where the vector is tumor cell-specific, proliferating smooth muscle-specific in tumor neovasculature, proliferating smooth muscle-specific in proliferating vascular lesion, proliferating mesangial cell-specific in glomerulonephritis, or proliferating myofibroblast-specific in fibrosis; where a DNA that encodes ribonucleotide reductase is deleted.

Further, embodiments of the present invention relate to: a method for expression/replication of a gene, protein or a peptide of a cell-specific expression/replication vector that does not target normal cells, by introducing the cell-specific expression/replication vector into living cells or tissue, to express and replicate; a method for suppressing the expression/replication of a gene, protein or a peptide of a cell-specific expression/replication vector that does not target normal cells, by introducing the cell-specific expression/replication vector into living cells or tissue, that have expressed and replicated, where said expression/replication is suppressed at a later desired period; the method for suppressing the expression/replication of a gene, protein or a peptide of a cell-specific expression/replication vector that does not target normal cells, where suppression comprises using antiviral drugs including aciclovir and ganciclovir; a method for detecting the in vivo distribution of a cell-specific expression/replication vector that does not target normal cells, by introducing into living cells or tissue, then expressed and replicated, and determining the thymidine kinase activity of said cell-specific expression/replication vector; and the method for detecting the in vivo distribution of a cell-specific expression/replication vector that does not target normal cells, where thymidine kinase activity is a determined by positron emission tomography using an uracil derivative FIAU labeled with $^{124}I$.

Still further, embodiments of the present invention relate to the method, where the cells and tissues in the organism are tumor tissues, vascular or lymphatic vessel constriction tissues, nephritic tissues or fibrotic tissues; a therapeutic drug having the cell-specific expression/replication vector that does not target normal cells; the therapeutic drug characterized by being a therapeutic drug against malignant tumor, fibrosis, proliferating vascular lesion or proliferating glomerulonephritis; the therapeutic drug characterized by being a therapeutic drug against malignant fibrous histiocytoma, gastrointestinal stromal tumor or uterine myoma; a therapeutic method for fibrosis and malignant tumor, where a proliferating myofibroblast is selectively disrupted as a result of replication of a vector, and expression of a gene, protein and a peptide, by introducing the cell-specific expression/replication vector that does not target normal cells into fibrotic tissues including lung and liver, or malignant tumor tissues including breast cancer, gastric cancer and pancreatic cancer, then; the therapeutic method for fibrosis and malignant tumor characterized by being a therapeutic method against malignant fibrous histiocytoma, gastrointestinal stromal tumor or uterine myoma; a therapeutic method for proliferating vascular lesion, where proliferating smooth muscle cells or perivascular cells are selectively disrupted as a result of replication of a vector, and expression of a gene, protein or a peptide, by introducing the cell-specific expression/replication vector that does not target normal cells into blood vessel or lymphatic vessel constriction tissues or arteriosclerotic tissues and tissues with diabetic retinopathy; a therapeutic method for proliferating glomerulonephritis, where proliferating mesangial cells are selectively disrupted as a result of replication of a vector, and expression of a gene, protein or a peptide, by introducing the cell-specific expression/replication vector that does not target normal cells into a nephritic tissue; the therapeutic method wherein the cell-specific expression/replication vector is administered to a vein or artery; the therapeutic method wherein the expression/replication of the cell-specific expression/replication vector is suppressed at a desired period; a method for producing a cell-specific expression/replication vector, by infecting a cell with a virus mixed solution after homologous recombination including the cell-specific expression/replication vector, where the transcriptional initiation regulatory region of a gene that expresses cell-specifically can be activated or a cell that expresses said gene, and the expression of a gene integrated in the vector is used as an index to purify to a single clone by limiting dilution without using agarose overlay assay; and the method for producing the cell-specific expression/replication vector where the cell is an ICP4 non-expressing cell.

BEST MODE OF CARRYING OUT THE INVENTION

As for the cell-specific expression/replication vector which does not target normal cells of the present invention, there is no particular limitation as long as it is a vector which does not target normal cells in which a transcriptional initiation regulatory region of a gene, specifically expressed in cells, is integrated upstream of a predetermined gene, wherein the thymidine kinase gene present in the cell-specific expression/replication vector is used to suppress its replication at a desired period. However, it is preferable for it to be an expression/replication vector specific to tumor cells, to proliferating smooth muscle cells in tumor angiogenesis, to proliferating smooth muscle cells in proliferating vascular lesion, proliferating mesangial cells in glomerulonephritis, or proliferating myofibroblasts in fibrosis. As a transcriptional initiation regulatory region of the gene specifically expressed in the cells mentioned above, a promoter region of a gene specifically expressed in cells or a partial region of this promoter can be exemplified, specifically, the examples include: a region including a base sequence from −260 to −219 of a calponin gene promoter of Seq. ID No. 1; a human calponin gene promoter comprising a base sequence shown in Seq. ID No. 2; a human calponin gene promoter comprising a base sequence of Seq. ID No. 3 and a region including a part of its structural gene. Furthermore, as for the transcriptional initiation regulatory region of a gene specifically expressed in cells, a base sequence where one or a few bases are deleted, substituted or added in the above-mentioned base sequence of Seq. ID No. 1, Seq. ID No. 2 or Seq. ID No. 3, having a regulating activity of transcriptional initiation, for example, a region including a homologous region to a calponin promoter derived from mouse, rat and pig can be exemplified.

As for the transcriptional initiation regulatory region of a gene specifically expressed in cells, other than the regions mentioned above, when proliferating smooth muscle cells are the targeted of an attack, the promoter region of SM22a gene (the sequence from −480 to −26 of the human SM22a gene; its homologous region of the SM22a gene derived from GenBank accession#D84342-D84344, mouse, rat or other mammals, may be used, and when endothelial cells are the target of a attack, a promoter region of Flk-1 or a promoter region of endothelial cell-specific genes such as the Flt-1 gene can be used. In these cases, a region including a part of a structural gene can also be made to be the transcriptional initiation regulatory region.

Another embodiment relates to linking an enhancer which significantly activates the transcription upstream of a transcriptional initiation regulatory region of a gene specifically expressed in the cells mentioned above. As for this enhancer, there is no specific limitation as long as it is an enhancer such as an enhancer of an adenovirus early gene, an enhancer of Moloney murine leukemia virus long terminal repeat, an enhancer of histone H2A gene, an enhancer of immunoglobulin, an enhancer of an insulin gene, an enhancer of a c-fos gene, an enhancer of the T-cell antigen receptor gene, an enhancer of the myopathic creatine kinase gene, a transcriptional enhancer of human 4F2 heavy-chain and the like. However, in the case where the transcriptional initiation regulatory region of a gene specifically expressed in cells is a region including a sequence from −260 to +73 of a promoter of a calponin gene, a 4F2 enhancer such as human 4F2 heavy-chain transcriptional enhancer (Seq. ID No. 4) the enhancer of a 4F2 heavy-chain gene, which is a membrane type-II glycoprotein, crossing the transmembrane structure only once is believed to be an activating factor of an amino acid transporter, which significantly enhances the transcription efficiency.

As for the predetermined gene useful for the construction of the cell-specific expression/replication vector, that does not target normal cells, there is no particular limitation as long as it is a gene necessary to initiate or maintain viral replication. For example, a viral replication-associated gene such as E1A gene of adenovirus, ICP6 (ribonucleotide reductase) gene and the like can be exemplified, such as, a gene (ICP4) that encodes a transcription factor necessary to initiate the replication of herpes virus. Furthermore, as for these genes, it may be a gene where a part or all of the original structural gene located downstream of the transcriptional initiation regulatory region is bound with the predetermined gene mentioned above in frame, and a DNA that encodes a fusion protein of a part of the N-terminal side of calponin protein with ICP4 protein can be specifically exemplified.

The cell-specific expression/replication vector which does not target normal cells, has a DNA that encodes a desired protein that is different from the predetermined gene is linked further downstream of the predetermined gene, and can express the desired protein under the control of the transcriptional initiation regulatory region. Specifically, a cell-specific expression/replication vector where the DNA that encodes the desired protein mentioned above is linked to a predetermined gene via IRES (internal ribosomal entry site; description of U.S. Pat. No. 4,937,190). A promoter of SM22a gene, a homologue of calponin, can also be linked to the IRES site. The present inventors are the first to clone a human SM22a promoter sequence and to report it (*J. Biochem.* (Tokyo) 122, 157-167, 1997), and the base sequence of the portion important for promoter activity (BamH I-DraI fragment 445 by of human SM22a promoter region) is indicated as Seq. ID No. 5. When the CMV promoter and the CAG promoter enhancer are used instead of IRES, a gene not under the control of the calponin promoter and encodes the desired protein may also be expressed in a cell type-nonselective manner.

Examples of the DNA that encodes the desired protein mentioned above are a gene related to the promotion of apoptosis, DNA that encodes a protein having an action to suppress neoangiogenesis, DNA that encodes a protein having an action to suppress cancer metastasis, DNA that encodes a protein having an action to suppress cancer and the like, and further two or more these examples may be linked. Examples of the gene related to the promotion of apoptosis mentioned above include: an apoptosis-promoting gene such as Bcl-xs, Bok/Mtd, Bcl-Gs/Bra, Bcl-GL, Bcl-Rambo, Hrk/DP5, Bik/Nbk/Blk, Bad, Bid, BimL, S, EL/BodL, M, S, Noxa/APR, Puma and the like; examples of the DNA that encodes a protein having an action to suppress neoangiogenesis include: DNA that encodes dominant negative receptor proteins such as angiostatin, endostatin, soluble Flk-1, soluble Flt-1, soluble FLT4, Tie1, Tie2 and the like; examples for the DNA that encodes a protein having an action to suppress cancer metastasis include: a DNA that encodes a protein such as matrix metalloprotease (MMP) inhibitor, bovine lactoferrin (bLF) and the like; examples of the DNA that encodes a protein having an action to suppress cancer include a DNA that encodes cell cycle suppressor such as p21, p16, p15 and the like or cell proliferation suppressor such as p53, Rb, IRF-1, APC and the like. These examples are not meant to be limiting.

The DNA that encodes the desired protein mentioned above, include a gene that encodes a marker protein such as EGFP cDNA and luciferase gene. A cell-specific expression/replication vector that can express these marker proteins is significantly useful in screening, detection, and the like.

As for the backbone of the viral vector used for the construction of the cell-specific expression/replication vector which does not target normal cells, it can be a vector that can be expressed by being infected in tumor cells such as osteosarcoma or soft tissue sarcoma, including leiomyosarcoma, gastrointestinal stromal tumor (GIST), malignant mesothelioma, malignant fibrous histiocytoma (MFH), fibrosarcoma, malignant meningioma, uterine myoma, neurinoma and the like, or proliferating smooth muscle cells or perivascular cells of tumor neovasculature, or introduction in a gene. As for the vector, an expression vector derived from a chromosome, an episome, a liposome and a virus can be exemplified. However, viral vector including papovavirus such as SV40, vaccinia virus, adenovirus, adeno-associated viral vector, fowl pox virus, pseudorabies virus, vector derived from retrovirus, herpes simplex virus vector (HSV vector) and the like maybe preferable, and among these, HSV vector and adenovirus vector, especially a conditionally replication-competent HSV vector or a conditionally replication-competent adenoviral vector maybe preferable from the viewpoint of the high efficiency of gene expression, the cytotoxic activity specific to proliferating cells, or the like. Using, for example, a vector where the DNA that encodes ribonucleotide reductase is deleted as the conditionally replication-competent HSV vector mentioned above, the cell-specific expression/replication vector which does not target normal cells and can control the replication of the vector and expression of the gene of the present invention can be preferably constructed.

As for the method of expression/replication of the cell-specific expression/replication vector that does not target normal cells, there is no particular limitation. As long as it is a method of expression/replication where the cell-specific expression/replication vector that does not target normal cells is directly introduced into living cells or tissue, such as a tissues or organs where tumors such as sarcoma in the bone or soft parts, leiomyosarcoma, gastrointestinal stromal tumor, malignant mesothelioma, malignant fibrous histiocytoma, fibrosarcoma, malignant meningioma, neurinoma and the like are developed, or by injecting the cell-specific expression/replication vector into the vascular system that nourishes the tumor; or where there is vessel constriction or arterial constriction after stent placement or organ transplantation, nephritic tissue, fibrosis tissue, or an organ including these tissues, or directly injecting the cell-specific expression/replication vector into the vessel using a stent or the like. The proliferating smooth muscles of the new tumor blood vessels are targeted for attack, by directly introducing or injecting the cell-specific expression/replication vector into the vascular system that nourishes the tumor, such as a malignant solid tumor. Further, as a method for expression/replication or suppression of a gene, a protein or a peptide of the cell-specific expression/replication vector that does not target normal cells, there is no particular limitation. As long as it is a method for suppressing the expression/replication of the cell-specific expression/replication vector, where the cell-specific expression/replication vector that does not target normal cells is expressed/replicated by introducing into living cells or tissue, an antiviral drug such as aciclovir, ganciclovir and the like, that maybe used later at a desired period. Furthermore, as for the therapeutic agent of the present invention, any kind of agent may be used as long as it comprises the cell-specific expression/replication vector that does not target normal cells as an active ingredient. Examples of the therapeutic drug include a therapeutic agent against living cells and tissue, such as malignant tumors, fibrosis, proliferating vascular lesion, proliferating glomerulonephritis, and the like.

As for the therapeutic method for treating fibrosis and malignant tumor, there is no particular limitation. As long as it is a method wherein the cell-specific expression/replication vector that does not target normal cells is introduced into fibrotic tissues, such as with pulmonary fibrosis and hepatic fibrosis, and malignant tumor tissues such as in breast cancer, gastric cancer and pancreatic cancer, causing a gene, a protein or a peptide to be expressed. Particularly, it is a method where only the proliferating myofibroblast is selectively disrupted, or where only the proliferating smooth muscle cells of tumor neovasculature or perivascular cells are selectively disrupted, is preferable. As for the method for introduction into the tissues where a malignant tumor has developed, it is a method for directly injecting the cell-specific expression/replication vector that does not target normal cells into the malignant tumor, or for injecting the cell-specific expression/replication vector into the tumor via perfusing vascular system, such as arterial or venous administration and the like. As for the therapeutic method for the proliferating vascular lesion of the present invention, there is no particular limitation. As long as it is a method where the cell-specific expression/replication vector that does not target normal cells is introduced into a lesion of vessel constriction or arteriosclerotic tissues and diabetic retinopathy tissues, and a gene, protein or peptide is expressed. A method where only the proliferating smooth muscle cells or perivascular cells are selectively disrupted can be exemplified. Further, as to the method for treating proliferating glomerulonephritis, there is no particular limitation. As long as it is a method where the cell-specific expression/replication vector that does not target normal cells is introduced into a lesion of glomerulonephritis, and a gene, a protein or a peptide is expressed. A method where only the proliferating mesangial cells are selectively disrupted can also be exemplified. Moreover, the therapeutic methods are characterized as a therapeutic method where the expression/replication of the cell-specific expression/replication vector is suppressed at a desired period, such as after the completion of the therapy.

As for the method for detecting the in vivo distribution of the cell-specific expression/replication vector that does not target normal cells, the method is characterized in that the cell-specific expression/replication vector that does not target normal cells is introduced into living cells and tissue, then expressed/replicated, to detect/determine the thymidine kinase activity of the cell-specific expression/replication vector. Specifically, the in vivo distribution of the cell-specific expression/replication vector can be detected by administering a uracil derivative FIAU labeled with $^{124I}$ into the organism, and detecting/determining the $^{124I}$ by Positron Emission Tomography (*Nature Med.* 7, 859-863, 2001).

As for the method for producing the cell-specific expression/replication vector that does not target normal cells, there is no particular limitation. As long as it is a method where a virus mixed solution after homologous recombination with, among others, the cell-specific expression/replication vector that does not target normal cells, is infected to (1) a cell where the regulatory region of a gene responsible for transcription initiation of that gene and cell-specificity can be activated or (2) a cell that expresses the gene, preferably an ICP4 non-expressing cell, and also the expression of the gene integrated in the vector is used as an index to purify to a single clone by limiting dilution. The cell-specific expression/replication vector that does not target normal cells can be obtained for the first time with the establishment of the method for producing the cell-specific expression/replication vector that does not target normal cells conducted by screening.

Embodiments of the present invention will be explained more specifically with the following examples, however, the scope of the invention will not be limited to these examples.

Example A

Methods and Materials

A-1 (Cells, Culture Methods, Antibodies and Viruses)

Human uterine leiomyosarcoma cell line SK-LMS-1 (HTB-88) and Vero cells (CCL-81) were purchased from American Type Culture Collection. Human osteosarcoma cell line OST (RCB0454) was purchased from RIKEN GENE BANK. For Vero E5 cells, the Vero cells wherein the ICP4 gene is transfected, those provided by N. Deluca (University of Pittsburgh School of Medicine, Pittsburgh) were used. For human malignant fibrous histiocytoma cell line (MFH-AI), those provided by Dr. Yanoma of Kanagawa Prefectural Cancer Center were used. As for the human gastrointestinal stromal tumor (GIST) cells and the human uterine myoma cells, tumor foci were aseptically prepared from the surgery specimen where the expression of calponin protein was confirmed by immunohistochemistry, treated with collagenase (1 mg/ml; Sigma Cat. #C-9722) solution, and the primary culture cells were separated. Those cells for vector infection experiment where 3 to 4 generations of subculture was conducted in an RPMI1640 medium were used. SK-LMS-1 was cultured in Eagle's MEM supplemented with 1 mM sodium pyruvate. OST, Vero cells and Vero E5 cells were cultured in DMEM. MFH-AI was cultured in RPMI1640 medium. All the media contain the following, respectively: heat-inactivated fetal bovine serum (Upstate Biotechnologies) at a final concentration of 10%; 2 mM L-glutamine; 100 units/mL penicillin; and 100 µg/mL streptomycin. Furthermore, all the cells mentioned above were cultured at 37° C. in a humidified atmosphere containing 5% $CO_2$.

The MFH-AI cells mentioned above were subcutaneously injected into the franks of six-week old female athymic nude mice (BALB/c Slc-nu/nu) (Japan SLC), and the tumors were fixed. The mice were dissected after two months, the tumor section that was aseptically excised from the metastasized foci in the lung, then treated with collagenase (1 mg/ml; Sigma Cat. #C-9722) and the cells were separated. The $1×10^6$ cells were injected into the tail vein of the six-week old female athymic nude mice. One month later, the individual tumor cells were separated from the tumor foci that metastasized again to the lung, in the same manner as described previously. This operation was repeated one more time, and the MFH-AI-LM cell line with high metastatic activity to lung was established.

The monoclonal antibody to HSV-1 or HSV-2 ICP4 protein (clone No. 1101) was purchased from the Goodwin Institute for Cancer Research. Immunoblot analysis was carried out in the same manner as previously described (*Int. J. Cancer* 79, 245-250, 1998). Chemiluminescence (ECL; Amersham Pharmacia Biotech) was used to visualize the bound antibodies, according to the manufacturer's protocol. Moreover, ICP4 deficient mutant HSV-1 d120 (*J. Virol* 56, 558-570, 1985) and ICP6 (ribonucleotide reductase)-deficient mutant HSV-1 hrR3, which were generated by low-multiplicity infections to ICP4-introduced Vero E5 cells or Vero cells, respectively, were kindly provided by Drs. N. Deluca and S. Weller (University of Connecticut Health Center, Farmington).

A-2 (RNA Preparation and RT-PCR Analysis)

Total RNA was extracted from cultured cells or tissues using the Isogene RNA extraction kit (Nippon Gene), and subjected to semi-quantitative RT-PCR analysis as described previously (*Int. J. Cancer* 79, 245-250, 1998). The conditions for PCR amplification were: a cycle of denaturation at 94° C. for 40 seconds, annealing at 60° C. for 30 seconds and extension reaction at 72° C. for 90 seconds was repeated 30 times. As a human calponin primer, 5'-gagtgtgcagacggaacttcagc-c-3' [forward primer 1 (FP1); nt#10-33 GenBank D17408; Seq. ID No. 6] and 5'-gtctgtgcccagcttggggtc-3' [reverse primer 1 (RP1); nt#660-680; Seq. ID No. 7] were used; as a primer of GAPDH (glyceraldehyde 3-phosphate dehydrogenase) as a control, 5'-cccatcaccatcttccagga-3' [forward primer 2 (FP2); nt#342-360; Seq. ID No. 8] and 5'-ttgtcataccaggaaatgagc-3' [reverse primer2 (RP2); nt#1052-1070; Seq. ID No. 9] were used, to amplify the DNA fragments of 671 bp and 731 bp, respectively.

A-3 (Isolation of the Human Calponin Promoter)

Genomic clones containing the 5' upstream region of the human calponin gene were isolated by screening a human genomic λEMBL3 phage library according to the method as previously described (*J. Biochem.* 120, 18-21, 1996). The 5'-end deleted fragments, p-1159Luc, p-385Luc, p-343Luc, p-310Luc, p-299Luc, p-288Luc, p-260Luc, p-239Luc, p-219Luc, p-201Luc, p-176Luc, p-153Luc were generated by PCR amplification, with the genomic clone as a template. Numbers indicate the 5' end of the DNA fragments are upstream from the ATG translational initiation codon, hereinafter referred to as +1. These deleted fragments have a common 3' end at position +73. The nucleotide sequence of the cloned fragments was determined by using a DQS-2000L DNA sequencer (SHIMADZU) according to the manufacturer's protocol, and it was confirmed that the sequence was identical to the sequence (DDBJ/GenBank™/EMBL database; accession No. D85611) as previously described (*J. Bio-*

*chem.* 120, 18-21, 1996). The minimum expression regulation region (−260 to +73) was identified by the method as previously described (*Cancer. Res.* 61, 3969-3977, 2001).

A-4 (Transfection and Luciferase Assay)

Cells cultured beforehand were divided and were plated onto a plate 24 hours before transfection. Cells ($5×10^4$) were transfected by injecting 1.2 µg of the promoter plasmid, 0.3 µg of the pCAGGS/β-gal-containing plasmid and 3.75 µl of FuGENET™6 transfection reagent (Roche) in each well of a 6-well dish, according to the manufacturer's protocol. Twenty-four hours after transfection, the cells were harvested in 100 µl/well of the cell lysis buffer (PicaGene™ Luciferase Assay System, Toyo Ink). After centrifugation at 4° C. at 12000 g for 5 minutes, the supernatants (20 µl or 30 µl) were used for luciferase assay and β-galactosidase assay, respectively. Luciferase activity was measured by using a BLR-201 luminescence reader (Aloka). The β-galactosidase assay was carried out by using β-galactosidase enzyme assay system (Promega) following the method as previously described (*J. Biochem.* (Tokyo) 122, 157-167, 1997). All experiments were repeated at least three times to confirm the reproducibility. By assaying β-galactosidase activity of the cell extracts, the transfection efficiency was determined, and luciferase activities (light units) were corrected according to the value. By comparing expression of the pSV2-Luc gene containing the SV40 enhancer and SV40 promoter, transfection efficiency of different cell lines was evaluated. Data are expressed as % for normalized absorbance±S.E. relative to the values of pSV2-Luc.

A-5 (Virus Preparation)

A 4.1 kb blunt-ended SalI-MseI fragment (provided by Dr. Hayward, Johns Hopkins School of Medicine) derived from pGH108 (*J. Virol.* 56, 558-570, 1985) containing an ICP4 coding region, was inserted into the blunt-ended BamHI site downstream of the 333 by human calponin promoter (−260 to +73) cloned to the pAMP1 plasmid, and a 444 by NotI fragment of the human 4F2 heavy-chain transcriptional enhancer (*Mol. Cell. Biol.* 9, 2588-2597, 1989) (provided by Dr. Leiden, Harvard Medical School) was subcloned to the SmaI site of said plasmid. The HindIII site at the 3' side of the pAMP1/CALP-ICP4 plasmid was blunted, the pIRES2-EGFP plasmid (Clontech) was double digested with BamHI and AflII, and the resulting 1576-bp fragment was subcloned. This BamHI-AflII fragment is composed of a IRES sequence (description of U.S. Pat. No. 4,937,190) and EGFP sequence (description of U.S. Pat. Nos. 5,625,048 and 5,804,387) as well as the SV40 derived poly A signal. Further, the 6.7-kb fragment obtained by double digestion of the pAMP1/CALP-ICP4-IRES2-EGFP plasmid with the use of EcoRI and SphI was blunted, and was subcloned into StuI blunted site of pKX2βG3 recombinant vector (pKX2βG3/CALP-ICP4-IRES2-EGFP). The pKX2βG3 recombinant vector (provided by Dr. Weller of the University of Connecticut) is comprised of a 2.3-kb XhoI fragment of the ICP6 coding sequence (pKpX2) in the pUC19 backbone, and the 3.0-kb *Eschericia coli* LacZ sequence is inserted into the BamH1 site of the ICP6 sequence (*J. Virol.* 62, 196-205, 1988).

Subsequently, the plasmid pKX2βG3/CALP-ICP4-IRES2-EGFP was linearized at XhoI site (one wherein the XbaI site at the 5' side of the ICP6 sequence of pKX2βG3 and the HindIII site at the 3' side of the ICP6 sequence are both substituted by XhoI site), and the pRRΔCALP-ICP4-IRES2-EGFP wherein the pUC19 sequence is eliminated and the d120 virus DNA were co-transfected to a subconfluent monolayer culture of ICP4 cDNA-transfected Vero E5 cells ($2.5×10^5$/well) in a 6-well tissue culture plate, by using Lipofectamine™ (GIBCO/BRL), according to the manufacturer's protocol. Three hours after the transfection, 1 ml of 20% FBS/DMEM culture solution was added, and the resultant transfected cells were cultured in the solution (10% FBS/DMEM) containing 0.5 mg/ml of 4-hydroxymethylbenzoic acid (HMBA) for 96 hours after the transfection. After confirmation of plaque formation, culture was further conducted for 24 hours with 10% of FBS/DMEM without HMBA. The cells were suspended in 500 µl/well of cold virus buffer (20 mM Tris-HCl containing 150 mM of NaCl; pH 7.5) and then frozen for conservation.

Freezing and thawing treatment with the combination of sonication (30 seconds for 3 times) was conducted three times, and the suspended cells in the solution mentioned above were lysed. The suspended cell solution was diluted stepwisely and infected to the subconfluent monolayer culture of SK-LMS-1 cells in a 96-well tissue culture plate. After the infection, culture was conducted for 96 hours in 100 µl/well of 1% FBS/DMEM containing 11.3 µg/ml of human IgG (Jackson ImmunoResearch Lab.). The wells where plaque formation was confirmed were screened with the expression of EGFP under a fluorescence microscope as an index. The SK-LMS-1 monolayer culture cells of the well containing EGFP positive-plaques were suspended in 100 µl of said culture solution, and 6 µl among them were used to determine the β-galactosidase enzyme activity with 5-bromo-4-chloro-3-indolyl-β-D-galactopyranoside (X-gal) as a substrate, by using a β-galactosidase enzyme assay system (Promega). The SK-LMS-1 cells suspended solution of a well that is positive for β-galactosidase enzyme activity was centrifuged for 5 minutes at 5000 rpm, and the pellet was re-suspended in 100 µl/well of cold virus buffer. Limiting dilution, infection and β-galactosidase enzyme activity determination conducted in the same manner using a 96-well tissue culture plate were repeated two times with the Vero E5 cells, and a recombinant viral vector d12•CALP•ΔRR was purified as a single plaque. After purification of the viral DNA, it was digested with the restriction enzyme XhoI, and recombination at the ribonucleotide reductase locus (ICP6 or RR-locus) was confirmed by Southern blotting with the XhoI fragment (2.3-kb) of ICP6 cDNA as a probe (FIG. 1).

Viruses were prepared by infecting Vero E5 cells in 10 to 20 bottles of 150 cm²/tissue culture flasks (IWAKI CLASS) and retrieving cells that were detached after 48 hours. Cells were collected by centrifugation at 4° C. for 5 minutes at 400×g, then suspended in 10 ml cold virus buffer (20 mM Tris-HCl containing 150 mM NaCl; pH 7.5). Freezing and thawing treatment with the combination of sonication (30 seconds for 3 times) were conducted three times, and the cells mentioned above were lysed. After centrifugation at 4° C. for 5 minutes at 1500×g, the supernatant was further centrifuged at 4° C. for 45 minutes at 15000×g. The resulting pellet was re-suspended in the cold virus buffer, and titers of the purified d12•CALP•ΔRR viral vector were determined by the plaque assay in Vero E5 cells.

A-6 (In Vitro Cytolysis Assay and Single Step Growth Assay)

The d12•CALP•ΔRR viral vector was infected to subconfluent monolayer culture of cells in a 6-well tissue culture plate at a multiplicity of infection (MOI) of 0.1 to 0.001 (pfu/cell) in 1% heat inactivated FBS/PBS. Said infected cells were incubated at 37° C. for 1 hour, and then cultured in said medium containing 1% FBS and 11.3 µg/ml of human IgG (Jackson ImmunoResearch Lab.). Forty-eight hours after the infection, the numbers of plaques/well were counted. For a single step growth assay, monolayer cultures of SK-LMS-1 cells or OST cells in 12-well tissue culture plates ($2×10^5$ cells/well) were infected with d12•CALP•ΔRR viral vector to a multiplicity of infection (MOI) of 0.1 in 1% FBS/PBS. The virus inoculum was removed after 1 hour, and the above-mentioned cells were incubated in the medium. The infected cells were harvested from the wells at the predetermined period (12 hours, 24 hours and 48 hours) with the use of 100 µl of the virus buffer. The cell suspension (1 µl) were diluted to $10^{-3}$, $10^{-4}$ and $10^{-5}$, and then plaque forming activity of viruses on Vero E5 cells were determined.

Further, the d12•CALP•ΔRR viral vector was infected to a subconfluent monolayer culture of MFH-AI-LM cells (cell lines with high metastatic activity to lung from human malignant fibrous histiocytoma MFH-AI cells) in a 6-well tissue culture plate at a multiplicity of infection (MOI) of 0.01/cell in 1% heat inactivated FBS/PBS. In addition, the d12•CALP•ΔRR viral vector was infected to a subconfluent monolayer culture of human GIST cells and cultured human uterine myoma cells in a 6-well tissue culture plate at a multiplicity of infection (MOI) of 0.1 or 0.01 (pfu/cell), respectively. The infected cells were incubated at 37° C. for 1 hour, and then cultured in said medium containing 1% FBS and 11.3 µg/ml of human IgG (Jackson ImmunoResearch Lab.). Seventy-two hours after the infection, X-Gal staining was conducted and the numbers of plaques/well were counted.

A-7 (Analysis of Sensitivity Against Ganciclovir, an Anti-Herpes Virus Agent of Viral Replication in Vitro)

The virus was infected to the subconfluent monolayer culture of SK-LMS-1 cells in a 24-well tissue culture plate ($5\times10^4$/well) or a 6-well tissue culture plate ($2.5\times10^5$/well) at a multiplicity of infection (MOI) of 0.01 (pfu/cell) in 1% heat inactivated FBS/PBS. The infected cells were incubated at 37° C. for 1 hour, and then cultured in a medium containing 1% FBS and 11.3 µg/ml of human IgG (Jackson ImmunoResearch Lab.), and various concentrations (0 to 1 µg/ml) of ganciclovir (Wako Pure Chemical Industries, Ltd.). Forty-eight hours after the infection, the numbers of plaques/well were counted.

For immunoblot analysis of ICP4 expression, d12•CALP•ΔRR viral vector or virus buffer alone was infected to the SK-LMS-1 cells and OST cells, respectively, to a multiplicity of infection (MOI) of 0.01 (pfu/cell), and was isolated after culture for 22 hours. The same amount of protein was subjected to 9% SDS-PAGE gel electrophoresis, and transferred to a nitrocellulose membrane (Bio-Rad). 5% skim milk (DIFCO Laboratories) was used to block the membrane at room temperature for two hours, and incubation was conducted overnight at 4° C. by using an anti-ICP4 antibody (dilution rate of 1:10000)

A-8 (Treatment in Vivo and Histological Analysis)

In order to study the therapeutic effect of intravenous administration of d12•CALP•ΔRR viral vector against human subdermally transplanted tumor xenografts, $1\times10^7$ human malignant fibrous histiocytoma MFH-AI cells were subcutaneously injected into the flank of six-week old female athymic nude mice (BALB/c Slc-nu/nu) (Japan SLC), and the tumors were fixed. After 19 days from the transplantation to the nude mice, the tumors developed from a diameter of approximately 6 mm to 7 mm (50 to 70 mm$^3$). 100 µl of virus suspension containing $1\times10^7$ pfu/mouse of d12•CALP•ΔRR viral vector (n=6), or the same amount of virus buffer (n=6) were injected into the tail vein once, by using a 30 gauge needle. The tumors were measured at a predetermined period after the injection, and the tumor volume was calculated according to the formula [$(0.53\times$length$\times$width$)^2$].

Further, in order to study the therapeutic effect of intravenous administration of d12•CALP•ΔRR viral vector against human lung metastatic tumor, $1\times10^6$ cells of the MFH-AI-LM cell line with a high metastatic activity to lung isolated from human malignant fibrous histiocytoma MFH-AI cells were injected once into the tail vein of six-week old female athymic nude mice (BALB/c Slc-nu/nu) (Japan SLC), and a lung metastatic tumor model was constructed. Fourteen days after intravenous injection of the MFH-AI-LM cells, 100 µl of the virus suspension containing $1\times10^7$ pfu/mouse of d12•CALP•ΔRR viral vector was intravenously injected once by using a 30 gauge needle, and the mice were sacrificed after 13 days. The whole lung metastasized tissues, the brain, liver, kidney, heart, small intestine, uterus and ovary were removed to use as specimens. These specimens were fixed with 2% paraformaldehyde, 0.5% glutaraldehyde, in PBS containing 1 mM MgCl$_2$ overnight at 4° C. Then, followed by X-Gal staining, the tumors were placed in a substrate solution, containing X-gal (1 mg/ml), 5 mM K$_3$Fe (CN$_6$), 5 mM K$_4$Fe (CN$_6$) and 1 mM MgCl$_2$ in PBS for 4 hours at 37° C., and then washed with PBS containing 3% DMSO. The specimens of the whole lung metastasized tissues were fixed in Bouin's solution [15% (v/v) saturated picric acid solution, 1.65% (v/v) formalin, and 1% (v/v) acetic acid/PBS] and embedded in paraffin. Sections of 4 µm thickness were mounted on a poly-L-lysine coated microslide, treated in xylene, and dehydrated through graded concentrations of alcohol solution. Then, hematoxylin-eosin staining was conducted, and the disruption by d12•CALP•ΔRR viral vector in the tumor tissues was observed by using an inverted microscope (Olympus BX-50).

Next, a lung metastatic tumor model was constructed by injecting $1\times10^6$ or $5\times10^5$ MFH-AI-LM cells into the tail vein of six-week old female athymic nude mice (BALB/c Slc-nu/nu) (Japan SLC). Seventeen days, 27 days and 34 days after intravenous injection of the MFH-AI-LM cells, 50 µl of virus suspension containing $1\times10^7$ pfu/mouse of d12•CALP•ΔRR viral vector was intravenously injected three times by using a 30 gauge needle, and the mice were sacrificed after 13 days. The whole lung metastasized tissues were removed, then fixed with 2% paraformaldehyde, 0.5% glutaraldehyde, in PBS containing 1 mM MgCl$_2$ overnight at 4° C. Then, the therapeutic effect by intravenous administration of the d12•CALP•ΔRR viral vector against human lung metastatic tumor was examined.

A-9 (Statistical Analysis)

Statistical differences were determined by using unpaired-Student's t-test. Differences were considered statistically significant with $p<0.05$.

Example B

Results

B-1 (Selective Replication of a Recombinant HSV Vector in Calponin-Positive Cells in Vitro)

To construct an HSV vector that replicates selectively in calponin-positive cells and proliferating cells, a DNA fragment containing the 4F2 enhancer/−260 calponin promoter/ICP4/IRES-EGFP was inserted into the RR (ICP6) locus (U$_{L36}$) of the ICP4-deficient HSV mutant d120 (*J. Virol.* 56, 558-570, 1985) by homologous recombination, and a d12•CALP•ΔRR viral vector was constructed. The d12•CALP•ΔRR viral vector expresses β-galactosidase under the control of an ICP6 promoter, and can express the ICP4 protein and EGFP protein under the control of calponin promoter (FIG. 1). The calponin-expressing human leiomyosarcoma cell line (SK-LMS-1) and calponin non-expressing human osteosarcoma cell line (OST) were used to evaluate the cell selectivity of the viral replication of d12•CALP•ΔRR viral vector.

Figure 2:
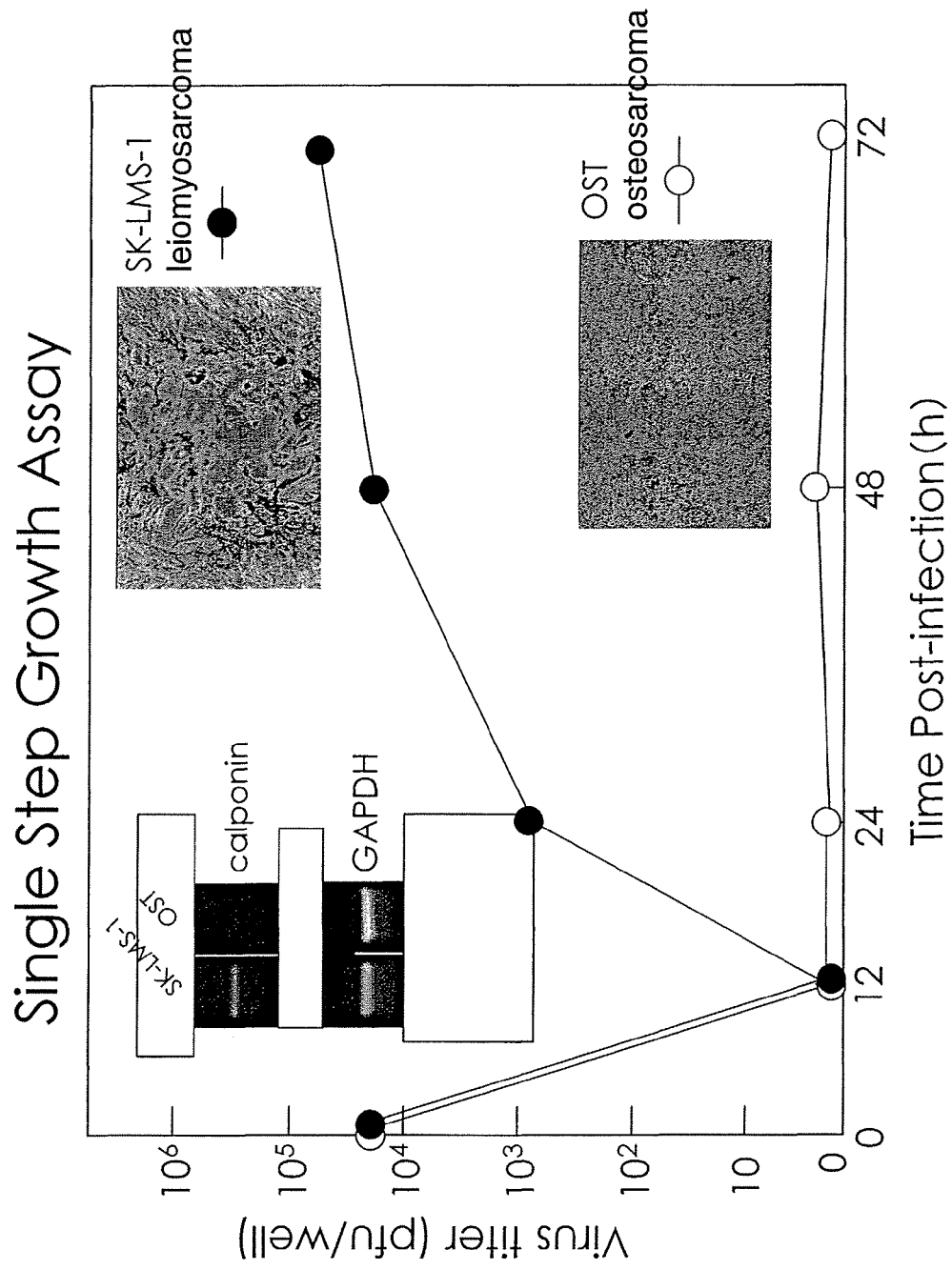
FIG. 2 shows the selective cytolytic activity of d12•CALPΔRR against calponin-positive malignant tumor cells (SK-LMS-1 leiomyosarcoma) in vitro. The view on the upper left shows the observation of calponin mRNA expression by RT-PCR. There is hardly any calponin expressed in OST osteosarcoma cells. The view on the right shows an X-Gal staining of the plaque.

Viral titers were assessed by single step growth assays of a multiplicity of infection (MOI) of 0.1 (pfu/cell) ($2\times10^5$ cells/well). The d12•CALP•ΔRR viral vector was replicated in calponin-positive SK-LMS-1 cells but the titers of the d12•CALP•ΔRR viral vector decreased in calponin-negative OST cells 72 hours after infection to approximately 1/100000 compared to those of the SK-LMS-1 cells (FIG. 2). The rate of proliferation of both cells was at the same level. By conducting immunoblot analysis of the cell extracts 22 hours after the infection, it was found that the ICP4 protein was expressed in SK-LMS-1 cells but not in OST cells. This was consistent with the result of the viral replication assay. In contrast, the d120 viral vector, which is the parental virus of homologous recombination, did not show generation of viral progenies at all in cultures of SK-LMS-1 and OST.

Figure 3:
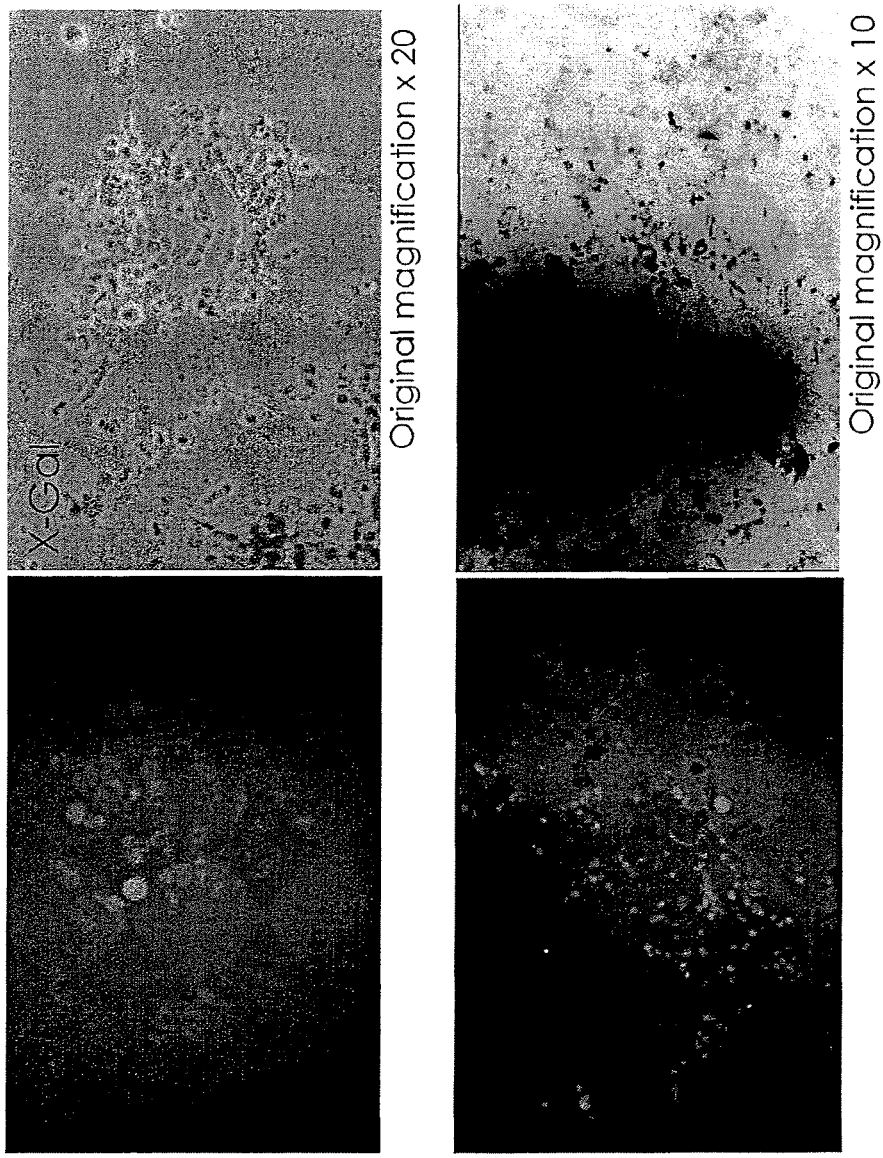
FIG. 3 shows the replication of d12•CALPΔRR in the calponin-positive malignant tumor cells (SK-LMS-1 leiomyosarcoma) in vitro with X-Gal staining which indicates the LacZ gene expression. The observation of EGFP protein that expresses under the control of a calponin promoter is made through a fluorescence microscope. Many cells expressing both LacZ and EGFP can be observed.

The d12•CALP•ΔRR viral vector was infected to the SK-LMS-1 cells in a 6-well dish, and after 96 hours from the infection, the β-galactosidase expressing cells were stained blue with X-gal agarose overlay, and the expression of EGFP was also examined at the same time with an inverted fluorescence microscope. It was confirmed that β-galactosidase was expressed in the tumor cells that are disrupted and almost abolished, and that EGFP-was expressed in the living cells around them (FIG. 3). There were a number of observations that both expressions occurred in one cell at the same time.

B-2 (Sensitivity to Ganciclovir, an Anti-Herpes Viral Agent, of Recombinant HSV-1 Vector)

Figure 4:
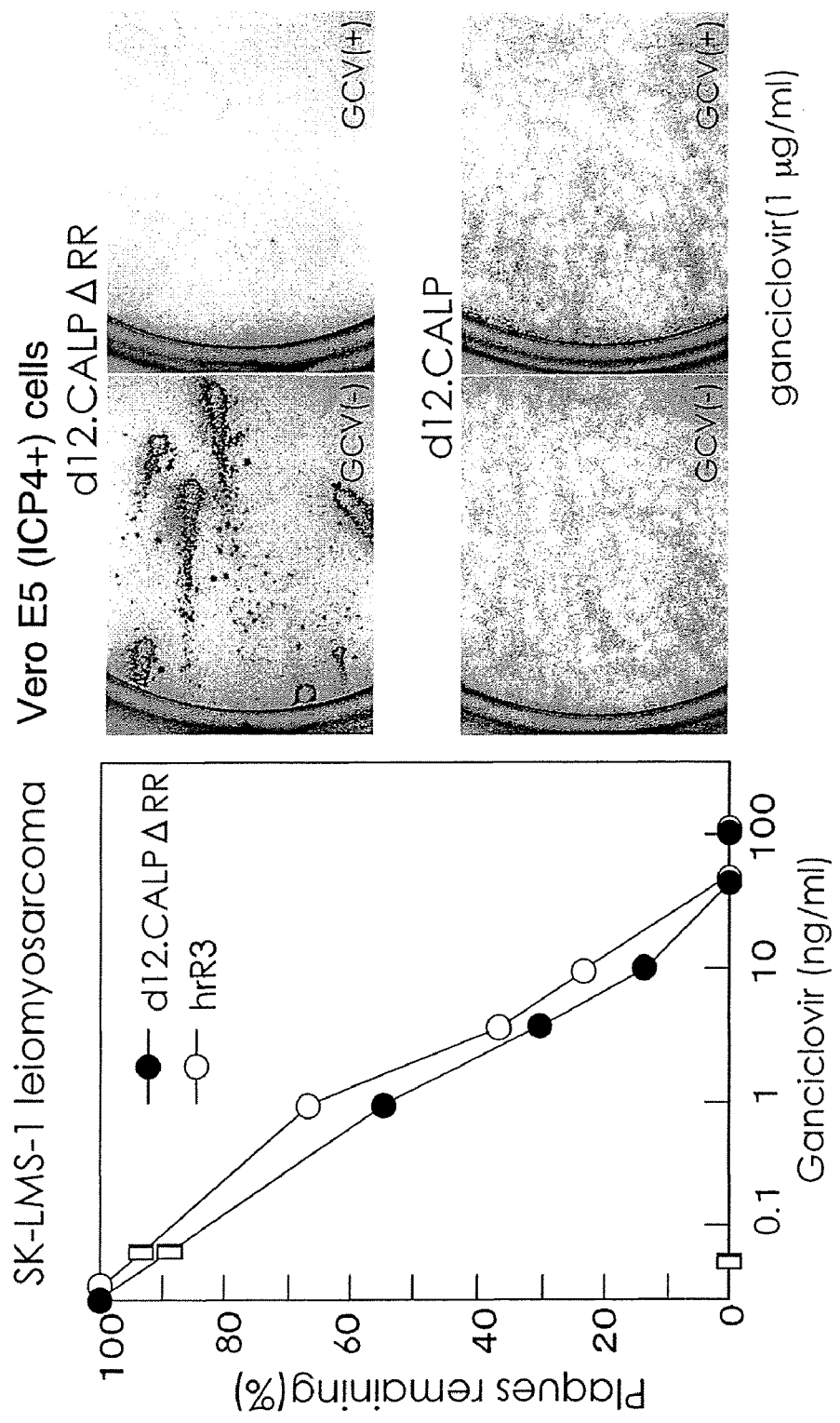
FIG. 4 shows the sensitivity of d12•CALPΔRR viral vector in the calponin-positive malignant tumor cells (SK-LMS-1 leiomyosarcoma) in vitro to various concentrations of ganciclovir in comparison to hrR3, which is known to be hypersensitive to ganciclovir. The view on the right shows d12•CALPΔRR viral vector replication in Vero E5 (ICP4+) cells in comparison with d12•CALP viral vector deficient in thymidine kinase (Japanese Patent Application No. 2001-143999), indicating the observation of the cytolytic activity under the presence of 1 μg/ml ganciclovir. d12•CALP is not sensitive to ganciclovir.

When the d12•CALP•ΔRR viral vector is applied to therapies for human malignant tumors, the most important property is that sensitivity to ganciclovir, an anti-herpes viral agent, is indicated since it has TK genes in an intact state. The d12•CALP•ΔRR viral vector was infected to SK-LMS-1 cells in a 24-well ($5\times10^4$/well) dish, in the presence of ganciclovir of various concentrations (0 to 100 ng/ml), at a multiplicity of infection (MOI) of 0.01 (pfu/cell). Forty-eight hours after the infection, the cells were stained with X-gal as a substrate, and the number of β-glactosidase-positive plaques per well was counted. Further, the d12•CALP•ΔRR viral vector was infected to Vero E5 cells ($2.5\times10^5$/well) in a 6-well dish in the presence and absence of 1 µg/ml ganciclovir, and 48 hours after the infection, the cells were stained with X-gal as a substrate (FIG. 4).

The replication of d12•CALP•ΔRR viral vector was suppressed in the presence of ganciclovir, for SK-LMS-1 cells and Vero E5 cells introduced with ICP4 cDNA. In SK-LMS-1 cells, the replication was completely suppressed in the presence of 40 ng/ml ganciclovir. The d12•CALP•ΔRR viral vector showed sensitivity to ganciclovir, which is equal to replicative HSV-1 mutant hrR3 that is reported to have stronger sensitivity to the drug agent than wild-type virus (*Cancer Res.* 54, 3963-3966, 2001). This result indicates that the d12•CALP•ΔRR viral vector has a safe measure in which viral infected cells can be eliminated by ganciclovir or aciclovir after therapy.

B-3 (In Vivo Treatment and Histological Analysis)

Figure 5:
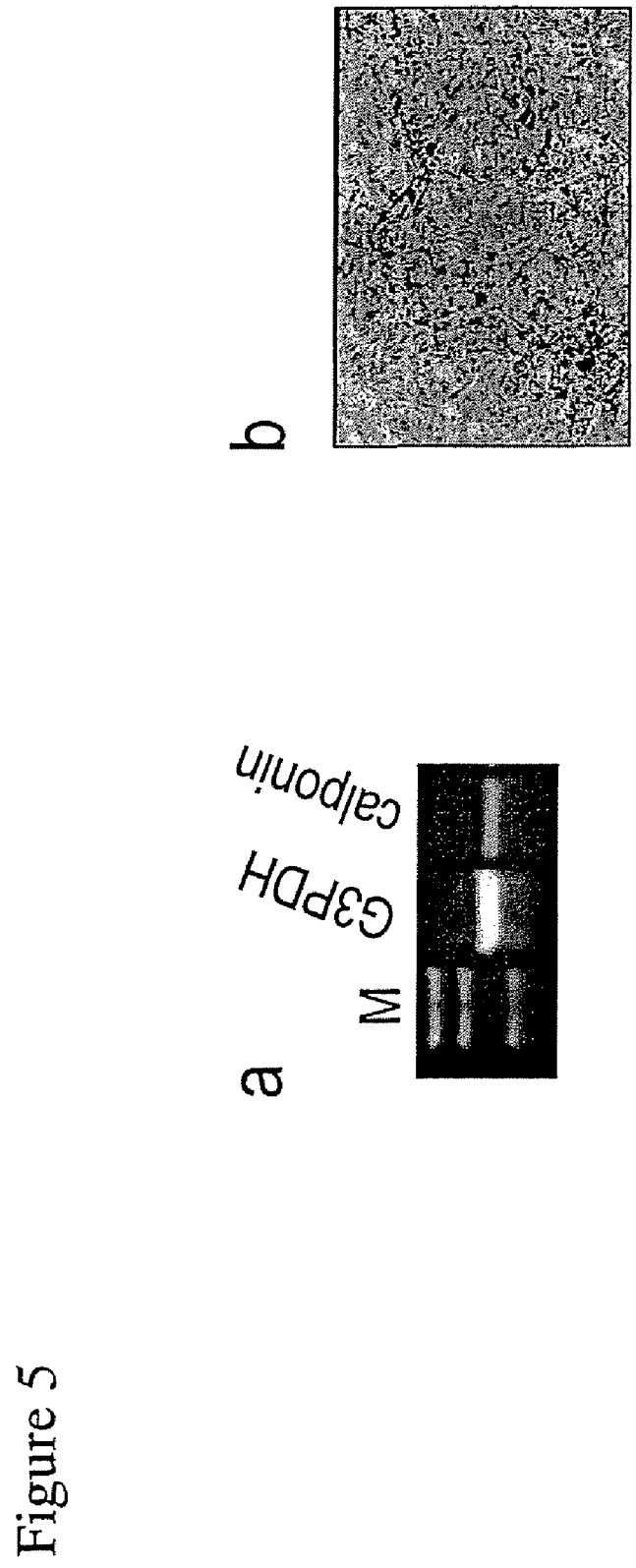
FIG. 5 shows the expression of calponin mRNA and the cell disruption assay or vector replication assay in vitro. (a) shows the expression of calponin (h1) mRNA in human sarcoma (malignant fibrous histiocytoma). (b) shows the X-Gal staining of plaque when infecting d12•CALPΔRR vector at 0.01 MOI to a tumor.
Figure 6:
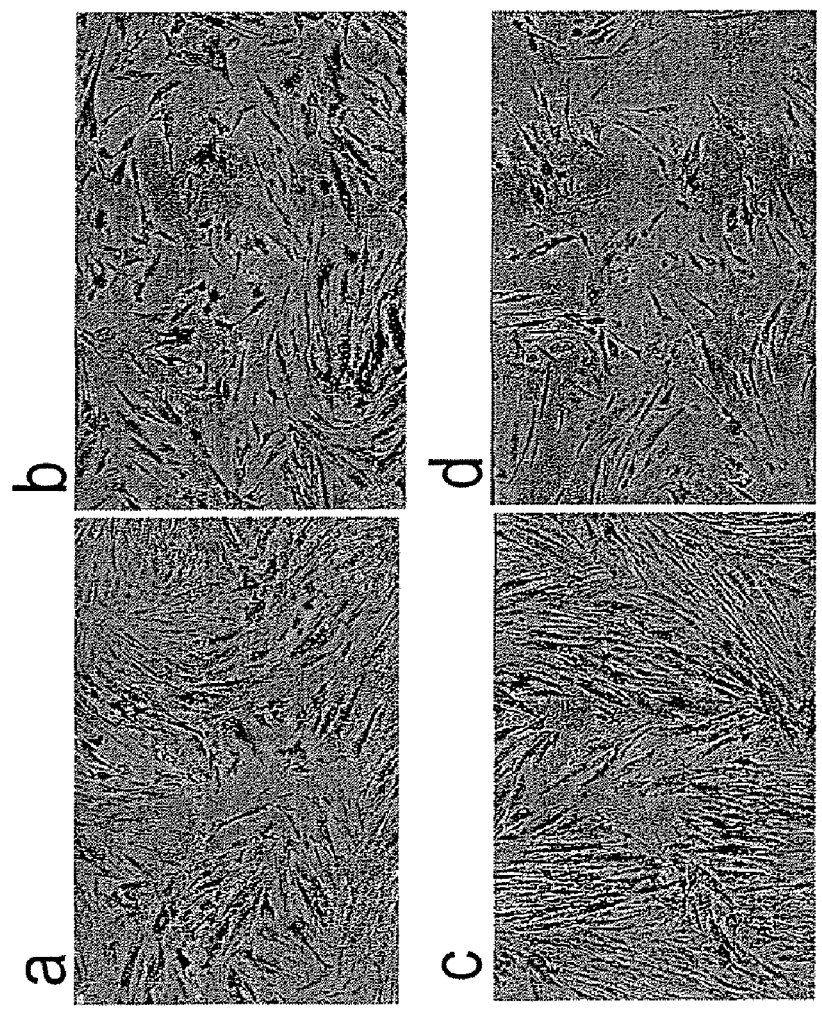
FIG. 6 shows the cell disruption assay and vector replication assay in vitro. It shows the X-Gal staining of plaque when infecting a d12•CALPΔRR vector to (a) GIST cells at 0.01 MOI, (b) GIST cells at 01 MOI, (c) to uterine myoma cells at 0.01 MOI, (d) to uterine myoma cells at 0.1 MOI, respectively.

RT-PCR analysis for total RNA of the MFH-AI-LM cell lines was conducted in order to examine whether MFH-AI-LM cell lines express the calponin mRNA, and it was confirmed that MFH-AI-LM cell lines express calponin mRNA (FIG. 5a). Further, the MFH-AI-LM cell lines mentioned above were infected with d12•CALP•ΔRR viral vector for 72 hours at a multiplicity of infection (MOI) of 0.01 (pfu/cell). The replication of the vector was stained with X-gal and evaluated with the plaque formation as an index (FIG. 5b). As a result, it was confirmed that the d12•CALP•ΔRR viral vector was replicated within the MFH-AI-LM cells, and that it shows cytolytic activity against MFH-AI-LM cells. Further, the d12•CALP•ΔRR viral vector was infected to cultured GIST cells and uterine myoma cells for 72 hours, respectively, at a multiplicity of infection (MOI) of 0.01 or 0.1 (pfu/cell). The replication of the vector was stained with X-gal and evaluated with plaque formation as an index (FIG. 6). As a result, it was confirmed that the d12•CALP•ΔRR viral vector is replicated within the cultured GIST cells (FIGS. 6a, 6b) and uterine myoma cells (FIGS. 6c, 6d), and from the results of 0.01 MOI (FIGS. 6a, 6c) and 0.1 MOI (FIGS. 6b, 6d), it was confirmed that the d12•CALP•ΔRR viral vector shows cytolytic activity in a dose-dependent manner. Particularly, in administration at 0.1 MOI (FIGS. 6b, 6d), the infection of d12•CALP•ΔRR viral vector to all the tumor cells was observed.

Figure 7:
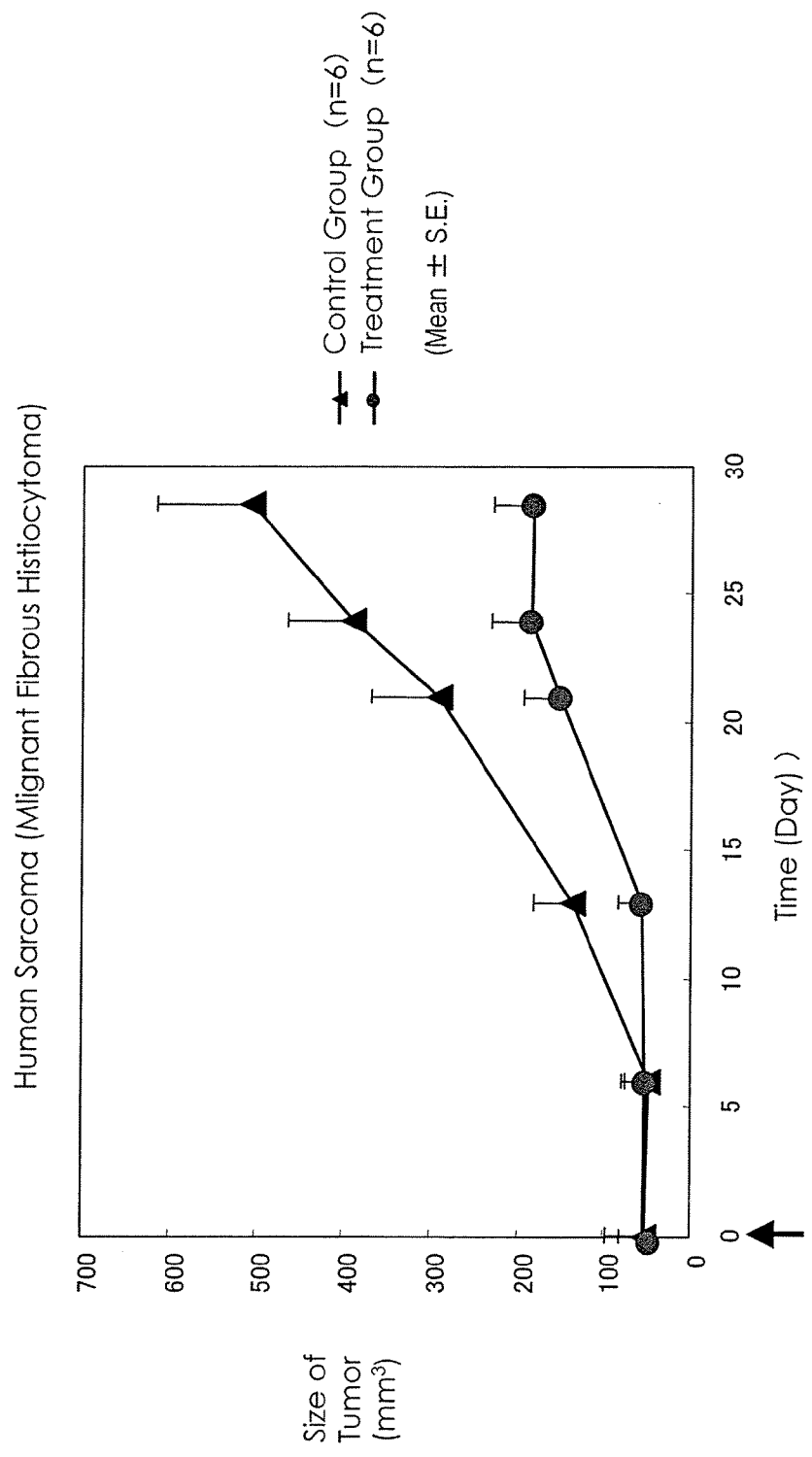
FIG. 7 shows a graph showing the anti-tumor effect against subcutaneous tumor xenografted in nude mice in vivo.

The in vivo anti-tumor effect of the d12•CALP•ΔRR viral vector against subdermally transplanted tumor xenografts that are isolated from MFH-AI cells was examined. The therapeutic effect by an intravenous injection of d12•CALP•ΔRR viral vector against subdermal transplanted tumors of the MFH-AI-LM cell lines is expressed as a chronological change (FIG. 7). On day 0, the d12•CALP•ΔRR viral vector of $1\times10^7$ pfu/mouse was infected into the tail vein. The tumor volume (means±S.E., n=6) of the group on day 29 after being treated with intravenous injection (d12•CALP•ΔRR viral vector administered) and the non-treated group (PBS administered) were 500±136 mm³ and 183±33 mm³, respectively. The treated group showed significant anti-tumor effect compared to the non-treated group.

Figure 8:
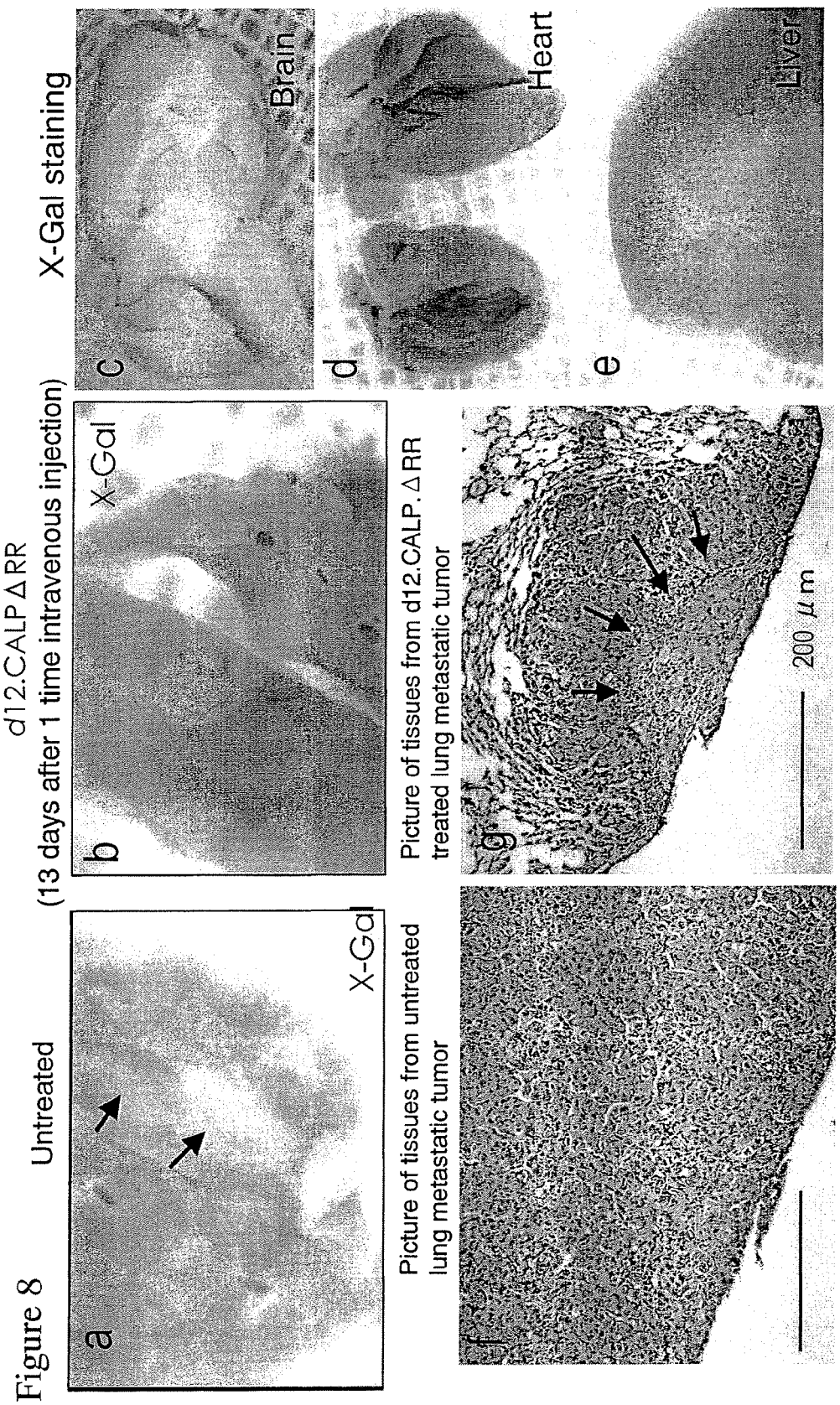
FIG. 8 shows the analysis of replication and the anti-tumor effect in a lung tumor metastasis in vivo by one intravenous administration of a d12•CALPΔRR vector.

The therapeutic effect of d12•CALP•ΔRR viral vector against human lung metastatic tumor by intravenous injection in vivo was examined (FIG. 8). The d12•CALP•ΔRR viral vector of $1\times10^7$ pfu/mouse was injected into the tail vein of a lung metastatic tumor model mouse where the MFH-AI-LM cells with high metastatic activity to lung isolated from human malignant fibrous histiocytoma MFH-AI cells were used, and metastases tumor in the lung at day 13 (FIGS. 8a, 8b) and the normal tissues, that is, the brain (FIG. 8c), heart (FIG. 8d), liver (FIG. 8e) excised at the same day were subjected to X-Gal staining. Histological analysis of lung metastatic tumor by hematoxylin-eosin staining (FIGS. 8f, 8g) was also conducted. By conducting an intravenous administration of d12•CALP•ΔRR viral vector, X-Gal staining which indicates replication of d12•CALP•ΔRR viral vector in the lung metastatic focus and histological tumor necrosis was observed. However, X-Gal staining that indicates the infection and replication of the d12•CALP•ΔRR viral vector in normal tissues such as the brain, heart and liver was not observed.

Figure 9:
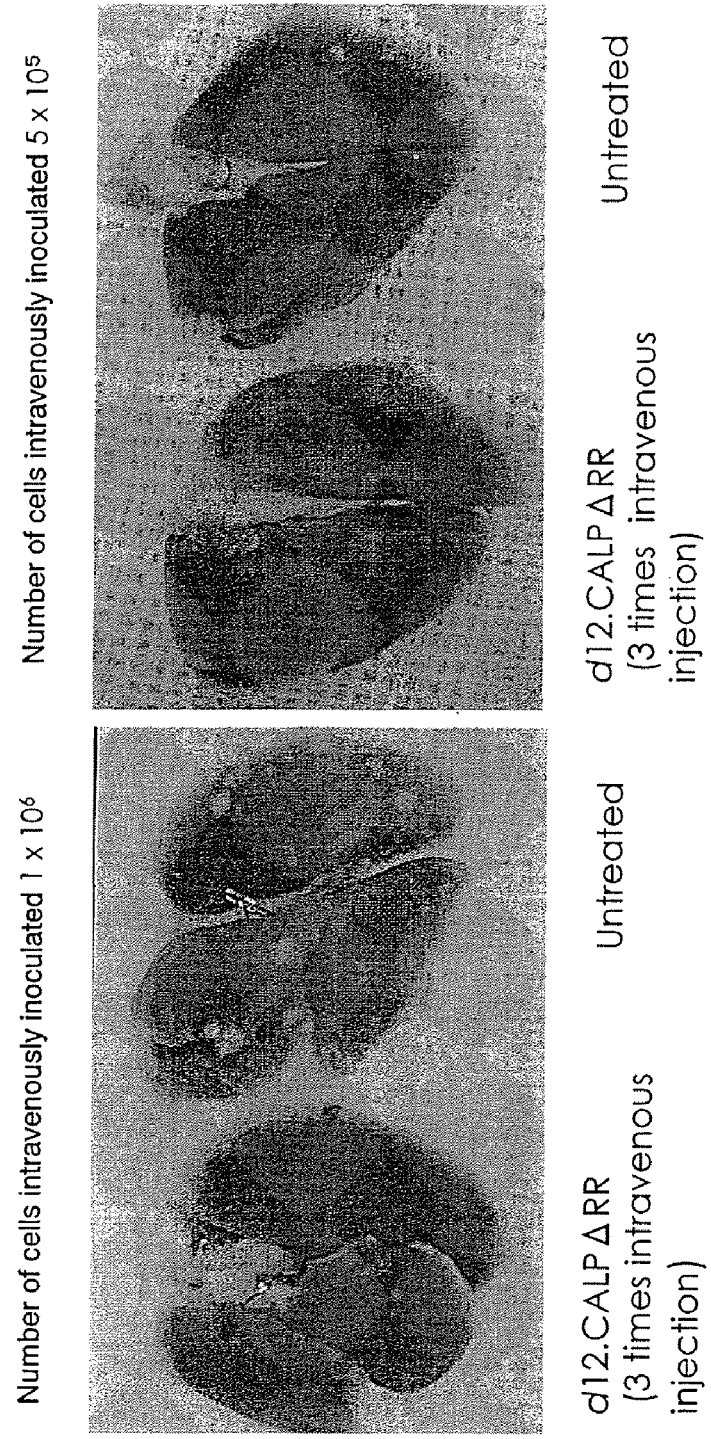
FIG. 9 shows the therapeutic effect of human lung metastatic tumor by three intravenous administrations of d12•CALPΔRR vector in vivo.

Subsequently, the therapeutic effect of human lung metastatic tumor where the number of MFH-AI-LM cells to be administered are set to $1\times10^6$ or $5\times10^5$, and the d12•CALP•ΔRR viral vector of $1\times10^7$ pfu/mouse was intravenously injected for a total of three times on day 17, day 27 and day 34 after administration of MFH-AI-LM cells was examined (FIG. 9). For all the lung metastatic tumor models constructed by injecting $1\times10^6$ or $5\times10^5$ of MFH-AI-LM tumor cells into the tail vein, the lung metastatic tumor-suppressing effect of the groups administered with d12•CALP•ΔRR vector was apparent. Moreover, the metastasis-suppressing effect of the treated group was also confirmed by the histological analysis by hematoxylin-eosin staining.

INDUSTRIAL APPLICABILITY

A malignant tumor derived from mesenchymal cells, that is a sarcoma, is resistant to chemotherapy or radiotherapy and continues to relapse even after surgical resection. With eventual metastasizing to the lung, liver, peritoneum and the like, the prognosis is quite poor. The number of cases in Japan is around 5000 annually, mainly including gastrointestinal stromal tumor (GIST) in the field of digestive surgery, bone or soft tissue sarcoma in the field of orthopedic surgery, and leimyosarcoma in the field of gynecology, malignant mesothelioma in the field of chest/digestive surgery, fibrosarcoma, malignant meningioma, malignant neurinoma in the field of neurosurgery and the like. Although it represents only about 1 to 2% of all cancers, it generates frequently in young people and there is no effective treatment modality except for some cases that have sensitivity to chemotherapy. Therefore the development of a new treatment modality is strongly required socially. The genetic analysis that is associated with the cause and pathology of sarcoma include the mutation of p53 and Rb gene in osteosarcoma and leimyosarcoma, the mutation of KIT gene in GIST, the presence of a fusion gene in Ewing sarcoma and synovial sarcoma and liposarcoma. However, sufficient therapies have not been. Further, in the animal experiments previously conducted, there have been attempts of direct introduction to sarcoma cells by using various vectors including p53 and cytokine, and herpes simplex virus thyidine kinase (HSV-tk) which is a suicide gene. However, sufficient therapeutical effect has not been obtained.

Gene therapy can increase the cancer cell selectivity at various levels, such as the cell-selective action of genes that are introduced to cancer cells, activity of expression promoters, and infection/introduction of viral vectors, and therefore is focused as a promising therapeutic method also for sarcoma. Indeed, it is reported that osteosarcoma-selective expression of HSV-tk in a non-replicative adenoviral vector by using an osteocalcin promoter can significantly suppress the lung metastatic focus also by intravenous administration (*Cancer Gene Ther.* 5, 274-280, 1998). However, since osteocalcin is also expressed in normal osteoblasts in the differentiation stage, it is not sufficient to increase the cancer cell-selectivity only by regulating the expression of a transgene. In addition, however, increasing the cell selectivity by promoters of marker genes for differentiation decreases the general purpose of the vector. For sarcomas that derive from various tissues and cells and have a limited number of cases, it is not advantageous based of cost-effectiveness for vector development.

Further, it is impossible to introduce therapeutic genes to all cancer cells with the use of the viral vectors and liposome vectors which are deficient for the replication ability, which have been used so far in experimental gene therapies against sarcomas. Therefore, although life extension can be obtained from animal experiments, continuous anti-tumor effect cannot be expected. Moreover, if the introduction efficiency of genes to cancer cells is low, the more viral vectors will be needed, and the risk of induction of excessive immunoreaction and allergic reaction will increase.

For treatment of intractable sarcomas, it has been believed that a completely novel approach that is different from that of the conventional methods is needed, however, no clues for such an approach was obtained. The examples of the present invention embody such requirements. The present invention can provide a cell-specific expression/replication vector that does not target normal cells, which replicates in particular cells such as malignant tumor cells and the like, not limited to sarcoma, and expresses specifically therapeutic genes while disrupting tumor cells. By using the cell-specific expression/replication vector that does not target normal cells, with a safety measure that can stop the replication of the virus with a drug agent after the completion of the therapy, a gene therapy using a cell-specific expression/replication vector for humans can be possible for the first time in the world.

The smooth muscle cells in the body mainly express the calponin gene. Since the proliferation of vascular smooth muscle cells is the cause of proliferating vascular lesions, such as tumor neoangiogenesis and blood vessel constriction after stent placement and diabetic retinopathy, therapies for these diseases become possible by selectively disrupting the proliferating smooth muscle cells with the use of the smooth muscle cell-specific expression/replication vector having a calponin promoter provided from the present invention. Among these, the therapeutic method which selectively disrupts the tumor vascular smooth muscles can now present an innovative effect as a therapeutic method for cancer that is effective to all solid cancers, because of the present invention. Further, it can effectively act as a therapeutic agent against proliferating glomerulonephritis which is caused by the proliferation of mesangial cells that express calponin, or fibrosis such as pulmonary fibrosis and hepatic fibrosis which is caused by the proliferation of myofibroblast that express calponin.

The invention claimed is:

1. A herpes simplex virus vector (HSV vector) that does not replicate in adult normal cells, but specifically replicates and is expressed in proliferating cells expressing calponin, and that is capable of suppressing its replication at a desired time by using the thymidine kinase gene, wherein the HSV vector is a recombinant HSV vector with a DNA fragment comprising:

(i) the promoter region of the human calponin gene consisting of the nucleotide sequence of SEQ ID NO.: 3;
(ii) an ICP4 gene encoding a transcription factor essential for initiation of a herpes viral replication operably linked downstream the promoter region of the human calponin gene,
(iii) an EGFP gene operably linked downstream the ICP4 gene via an internal ribosomal entry site; and
(iv) a LacZ gene integrated upstream to the said promoter region of the human calponin gene;

wherein the DNA fragment is inserted by homologous recombination into the ribonucleotide reductase gene locus of an HSV vector that comprises an endogenous thymidine kinase gene and lacks functional endogenous ICP4 gene, and wherein the expression of both the LacZ gene and the EGFP gene is used to identify the recombinant HSV vector.

2. The HSV vector according to claim 1, wherein an enhancer is operably linked upstream to the promoter region of the human calponin gene.

3. The HSV vector according to claim 2, wherein the enhancer is a 4F2 enhancer.

4. A therapeutic composition comprising the HSV vector according to claim 1 wherein the proliferating cells are smooth muscle cells.

5. The recombinant HSV vector of claim 1, further comprising a heterologous gene encoding a protein or a peptide of interest.

6. A method for expressing a gene, protein or a peptide comprising introducing the HSV vector according to claim 5 into the cells and tissues of an organism, then expressing the gene, protein, or peptide of the vector.

7. A method for suppressing the expression of a gene, protein or a peptide of the HSV vector according to claim 5 comprising,
   (i) introducing the HSV vector according to claim 5 into the cells and tissues of an organism,
   (ii) expressing the gene, protein or peptide of the vector, and
   (iii) suppressing the expression of the gene, protein or peptide at a later desired time by administering an antiviral drug, wherein said antiviral drug is aciclovir or ganciclovir.

8. The method according to any one of claim 6 or 7, wherein the cells and tissues in the organism are tumor tissues, vascular or lymphatic vessel constriction tissues, nephritic tissues or fibrotic tissues.

9. A method for producing a cell-specific recombinant HSV vector that does not replicate in adult normal cells, but replicates and is expressed specifically in a proliferating cells that express calponin, and that is capable of suppressing its replication at a desired time by using the thymidine kinase gene, said method comprising the steps of:
   (a) preparing a DNA fragment comprising,
       (i) the promoter region of the human calponin gene consisting of the nucleotide sequence of SEQ ID NO.: 3,
       (ii) an ICP4 gene encoding a transcription factor essential for initiation of HSV replication operably linked downstream the promoter region of the human calponin gene,
       (iii) an EGFP gene operably linked downstream the ICP4 gene via an internal ribosomal entry site, and
       (iv) a LacZ gene integrated upstream the promoter region of the human calponin gene,
   (b) contransfecting the DNA fragment with an HSV vector that comprises an endogenous thymidine kinase gene and lacks functional endogenous ICP4 gene into a cell in which the promoter region of the human calponin gene consisting of the nucleotide sequence of SEQ ID NO.: 3 can be activated; wherein the DNA fragment is inserted by homologous recombination into the ribonucleotide reductase gene locus of the HSV vector to produce HSV recombinant vectors, and
   (c) selecting a single clone of recombinant HSV vector expressing both LacZ and EGFP genes via screening the HSV recombinant vectors by limiting dilution without agarose overlay assay using both the LacZ gene and the EGFP gene as markers.

10. The method for producing the HSV vector according to claim 9, wherein the cell is an ICP4 (−) cell.

* * * * *

UNITED STATES PATENT AND TRADEMARK OFFICE
CERTIFICATE OF CORRECTION

PATENT NO. : 7,785,870 B2 Page 1 of 1
APPLICATION NO. : 10/500173
DATED : August 31, 2010
INVENTOR(S) : Katsuhito Takahashi and Hisako Yamamura It is certified that error appears in the above-identified patent and that said Letters Patent is hereby corrected as shown below:

In Claim 8, line 1 (Col. 27, line 16) delete "any one of claim 6 or 7" and insert --any one of claim 5 or 6--.

Signed and Sealed this

Sixteenth Day of November, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 41
<212> TYPE: DNA
<213> ORGANISM: Homo sapiens

<400> SEQUENCE: 1
gaaacaatga cacaatcagc tcccaatacc aagggcctga c                41

<210> SEQ ID NO 2
<211> LENGTH: 260
<212> TYPE: DNA
<213> ORGANISM: Homo sapiens
```

<400> SEQUENCE: 2

```
gaaacaatga cacaatcagc tcccaatacc aagggcctga catcacaagg ggaggggaag      60
gcagctgagg ttgtgggggg aggtgccccg cccttggca ggcccctaca gccaatggaa     120
cggccctgga agagacccgg gtcgcctccg gagcttcaaa acatgtgag gagggaagag     180 tgtgcagacg gaacttcagc cgctgcctct gttctcagcg tcagtgccgc cactgccccc    240
gccagagccc accggccagc                                                 260
```

<210> SEQ ID NO 3
<211> LENGTH: 333
<212> TYPE: DNA
<213> ORGANISM: Artificial Sequence
<220> FEATURE:
<223> OTHER INFORMATION: Description of Artificial Sequence: Region
      consist of human calponin gene promoter and its structural
      gene fragment

<400> SEQUENCE: 3

```
gaaacaatga cacaatcagc tcccaatacc aagggcctga catcacaagg ggaggggaag      60
gcagctgagg ttgtgggggg aggtgccccg cccttggca ggcccctaca gccaatggaa     120
cggccctgga agagacccgg gtcgcctccg gagcttcaaa acatgtgag gagggaagag     180 tgtgcagacg gaacttcagc cgctgcctct gttctcagcg tcagtgccgc cactgccccc    240
gccagagccc accggccagc atgtcctctg ctcacttcaa ccgaggccct gcctacgggc    300
tgtcagccga ggttaagaac aaggtagggg tgg                                 333
```

<210> SEQ ID NO 4
<211> LENGTH: 445
<212> TYPE: DNA
<213> ORGANISM: Homo sapiens

<400> SEQUENCE: 4

```
gtgagtgcag cgcgcccccg tcccgggtac ctccggttga atctggtggc ttgcaccgac      60
cccctcccct gtcccagac ggatctagat ggttcttccc tccatcccgt accgacgact     120 gtccccctt cccccacccc ctccccggca cattgtcctt ccctcctttc tttgaagaaa     180 gccgaccgc ccctcactcc gtcacgaggg tgggtgactc agcgtcctcc ttcccgcgg     240 cgccagaagc cagttgcaac cggtttctga agtaatgtgc aggactcctt acatcagctc    300
ctctgagtct cgtgattcag ccttgcctcc ctctctcccc ctttgccccc tccccgtccc    360
acccttaggc gctgggagaa gggagggtgg ggaggtcagg ggcctctcag aggggcctca    420
cttgttaacc cagcccccat ttcag                                          445
```

<210> SEQ ID NO 5
<211> LENGTH: 455
<212> TYPE: DNA
<213> ORGANISM: Homo sapiens

<400> SEQUENCE: 5

```
ggatcccatg tccatcaga gctaaaagcc ccaggaggag agggtggctg gtttgtcccc      60
acaaacccct gggattcccg gctccccagc cccttgcccc tctctccagc cagactctat    120
tgaactcccc ctcttctcaa actcggggcc agagaacagt gaagtaggag cagccgtaag   180
tccgggcagg gtcctgtcca taaaaggctt ttcccgggcc ggctcccgc cggcagcgtg     240 ccccgccccg gccgctccaa tctccaaagc atgcagagaa tgtctcggca gccccggtag    300
```

-continued

```
actgctccaa cttggtgtct ttccccaaat atggagcctg tgtggagtca ctgggggagc    360
cgggggtggg gagcggagcc ggcttcctct agcagggagg gggccgagga gcgagccagt    420
gggggaggct gacatcacca cggcggcagc ccttt                               455
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:FP1

<400> SEQUENCE: 6
gagtgtgcag acggaacttc agcc                                            24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:RP1

<400> SEQUENCE: 7
gtctgtgccc aacttggggt c                                               21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:FP2

<400> SEQUENCE: 8
cccatcacca tcttccagga                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:RP2

<400> SEQUENCE: 9
ttgtcatacc aggaaatgag c                                               21